(12) United States Patent
Alt et al.

(10) Patent No.: US 9,242,069 B2
(45) Date of Patent: Jan. 26, 2016

(54) METHOD FOR CONTROL OF STEM CELL INJECTION INTO THE BODY

(75) Inventors: Eckhard Alt, Ottobrunn (DE); Kai Pinkernell, Muenster (DE); Russ Auger, Chicago, IL (US)

(73) Assignee: SCICOTEC GmbH, Grünwald (DE)

(*) Notice: Subject to any disclaimer, the term of this patent is extended or adjusted under 35 U.S.C. 154(b) by 1756 days.

(21) Appl. No.: 11/068,495

(22) Filed: Feb. 28, 2005

(65) Prior Publication Data

US 2005/0226855 A1 Oct. 13, 2005

Related U.S. Application Data

(63) Continuation-in-part of application No. 10/955,403, filed on Sep. 30, 2004, now Pat. No. 7,452,532, which is a continuation-in-part of application No. 09/968,739, filed on Sep. 30, 2001, now Pat. No. 6,805,860.

(51) Int. Cl.
*A61M 25/00* (2006.01)
*C12N 5/077* (2010.01)
*A61K 35/12* (2015.01)

(52) U.S. Cl.
CPC ......... *A61M 25/0023* (2013.01); *C12N 5/0657* (2013.01); *A61K 35/12* (2013.01); *C12N 2501/165* (2013.01); *C12N 2502/21* (2013.01); *C12N 2506/21* (2013.01)

(58) Field of Classification Search
None
See application file for complete search history.

(56) References Cited

U.S. PATENT DOCUMENTS

| | | | | |
|---|---|---|---|---|
| 4,526,574 A | * | 7/1985 | Pekkarinen | 604/505 |
| 4,552,554 A | * | 11/1985 | Gould et al. | 604/506 |
| 4,583,974 A | * | 4/1986 | Kokernak | 604/211 |
| 4,863,429 A | * | 9/1989 | Baldwin | 604/135 |
| 6,551,302 B1 | * | 4/2003 | Rosinko et al. | 604/505 |
| 2005/0101599 A1 | * | 5/2005 | Zeiher et al. | 514/227.5 |

OTHER PUBLICATIONS

"Pancreas Islet Cells can be Injected Through the Hepatic Vein of the Liver," article from Internal Medicine News, Jul. 1, 2003.
Abraham A et al., "Human Pancreatic Islet-Derived Progenitor Cell Engraftment in Immunocompetent Mice," American Journal of Pathology, 164:817-30,2004.
Anglani et al., "In Search of Renal Stem Cells," G. Ital. Nefrol19, 6:607-616, 2002.
Barbash et al., "Systematic Delivery of Bone Marrow-Derived from Mesenchymal Stem Cells etc.," Circulation, 108:863-68, 2003.
Blau et al, "The Evolving Concept of a Stem Cell: Entity or Function?," Cell (105:829-41, Jun. 29, 2001).
Bonner-Weir et al., "Pancreatic Stem Cells" J. Pathology 197 (4): 519-26 (2002).
Borisov A. B. et al., "Proliferative potential and differentiated characteristics of cultured cardiac muscle cells expressing the SV 40 T oncogene," Card Growth Reg 1995; 752:80-91.
Braunwald E. et al., "Myocardial reperfusion, limitation of infarct size, reduction of left ventricular dysfunction, and improved survival: should the paradigm be expanded?," Circulation 1989; 79:441-4.
Claycomb W. C. et al., "Culture of the terminally differentiated adult cardiac muscle cell: A light and scanning electron microscope study," Dev Biol 1980;80:466-482.
Claycomb W. C. et al., "HL-1 cells: A cardiac muscle cell line that contracts and retains phenotypic characteristics of the adult cardiomyocyte," Proc Natl Acad Sci USA 1998; 95:2979-84.
Delcarpio J. B. et al., "Morphological characterization of cardiomyocytes isolated from a trans-plantable cardiac tumor derived from transgenic mouse atria (AT-1 cells)," Circ Res 1991; 69(6):1591-1600.
Galli R et al., "Skeletal myogenic potential of human and mouse neural stem cells," Nat Neurosci 2000;3:986-991.
Goldstein M. A. et al., "DNA synthesis and mitosis in well-differentiated mammalian cardiocytes," Science 1974; 183:212-3.
Gompe, "Liver Repopulation for the Treatment of Metabolic Diseases," J. Inherited Metabolic Disease 24, 2:231-44, 2001.
Jackson K. A. et al., "Regeneration of ischemic cardiac muscle and vascular endothelium by adult stem cells," J Clin Invest 2001; 107(11): 11395-402.
Kehat 1. et al., "Human embryonic stem cells can differentiate into myocytes with structural and functional properties of cardiomyocytes," J Clin Invest 2001; 108:407-14.
Kinnaird T et al., "Local Delivery of Marrow-Derived Stromal Cells Augments Collateral Perfusion Through Paracrine Mechanisms," Circulation, 109: 1543-49, 2004.
Kline R. P. et al., "Spontaneous activity in transgenic mouse heart: Comparison of primary atrial tumor with cultured AT-1 atrial myocytes," J Cardiovasc Electrophysiol 1993; 4(6):642-660.
Klug M. G. et al., "Genetically selected cardiomyocytes from differentiating embryonic stem cells form stable intracardiac grafts," J Clin Invest 1996; 98(1):216-24.
Kocher A. A. et al., "Neovascularization of ischemic myocardium by human bonemarrow-derived angioblasts prevents cardiomyocyte apoptosis, reduces re-modeling and improves cardiac function," Nat Med 2001; 7(4):430-6.

(Continued)

*Primary Examiner* — Blaine Lankford

(57) ABSTRACT

A method is described for repairing tissue of a selected organ from among heart, brain, liver, pancreas, kidney, and glands in a patient's body. In the method, stem cells that have the capability to repair tissue of the selected organ are intraluminally applied through a designated natural body vessel or duct leading to a predetermined target site of the tissue of the selected organ to be repaired. The stem cells are delivered into the respective vessel or duct through a catheter having a proximal portion of relatively larger central lumen diameter and outer diameter, and a distal portion of relatively smaller central lumen diameter and outer diameter, the two portions being integral with one another so that stem cells delivered into the central lumen of the proximal portion will flow through and exit the central lumen of the distal portion, the lumen diameter and length of each of the two portions being selected to minimize the pressure drop across the catheter during flow of the stem cells.

25 Claims, 8 Drawing Sheets

(56) References Cited

OTHER PUBLICATIONS

Kopen G et al., "Marrow Stromal Cells Migrate Throughout Forebrain and Cerebellum, and they Differentiate into Astrocytes After Injection into Neonatal Mouse Brains," Proc. Natl. Acad. Sci. USA. 96:10711-16,1999.

Lanson Jr. N. A. et al., "Gene expression and atrial natriuretic factor processing and secretion in cultured AT-1 cardiac myocytes," Circulation 1992; 85(5): 1835-1841.

Lee J. S. et al., "Gene therapy for therapeutic myocardial angiogenesis: A promising synthesis of two emerging technologies," Nat Med 1998; 4(6):739-42.

Makino S. et al., "Cardiomyocytes can be generated from marrow stromal cells in vitro," J Clin Invest 1999; 103:697-705.

Masuya M et al., "Hematopoietic Origin of Glomerular Mesangial Cells" Blood, 101, 6:2215-18,2003.

Olanow, "Surgical Therapy for Parkinson's Disease," Eur. J. Neurol. 9,3:31-39,2002.

Orlic D. et al., "Bone marrow cells regenerate infarcted myocardium," Nature 2001; 410:701-5.

Ostenfeld et al., "Recent Advances in Stem Cell Neurobiology," Advances and Technical Standards in Neurosurgery, 28:3-89,2003.

Prockop D. J. et al., "Marrow stromal cells for non hematopoetic stem tissues," Science 1997; 276:71-74.

Rangappa et al., "Transformation of Adult Mesenchymal Stem Cells Isolated from the Fatty Tissue etc.," Ann Thorac. Surg. 75:775-79,2003.

Reubinoff B et al., "Neural Progenitors from Human Embryonic Stem Cells," Nature Biotechnology, 19: 1134-40,2001.

Rosenthal N, "Prometheus's Vulture and the Stem-Cell Promise" N. Engl. J. Med. 349:267-74, 2003.

Schomig A. et al., "Coronary stenting plus platelet glycoprotein IIb/IIIa blockade compared with tissue plasminogen activator in acute myocardial infarction," N Engl J Med 2000; 343:385-391.

Scorsin M. et al., "Comparison of the effects of fetal cardiomyocyte and skeletal myoblast transplantation on postinfarction left ventricular function," J Thorac Cardiovasc Surg 2000; 119:1169-75.

Stedman's Medical Dictionary, 27th Edition, duct, 2003.

Study re "Stem Cells Hold Promise for Treating Disease," Journal of Tissue Engineering, Jan. 26, 2002.

Sussman, "Heart and Bones," Letters to Nature 410:640-641, 2001.

Taylor D. A. et al., "Regenerating functional myocardium: Improved performance after skeletal myoblast transplantation," Nat Med 1998; 4(8):929-33.

Thomson J. A. et al., "Isolation of a primate embryonic stem cell," Proc Natl. Acad Sci USA 1995; 92:7844-48.

Watanabe E. et al., "Cardiomyocyte transplantation in a porcine myocardial infarction model," Cell Transplant 1998; 7(3):239-246.

Watanabe E. et al., "Effect of basic fibroblast growth factor on angiogenesis in the infarcted porcine heart," Basic Res Cardiol 1998; 93:30-7.

Zuk P. A. et al., "Multilineage cells from human adipose tissue: Implications for cell-based therapies," Tiss Engin 2001; 7(2):211-28.

\* cited by examiner

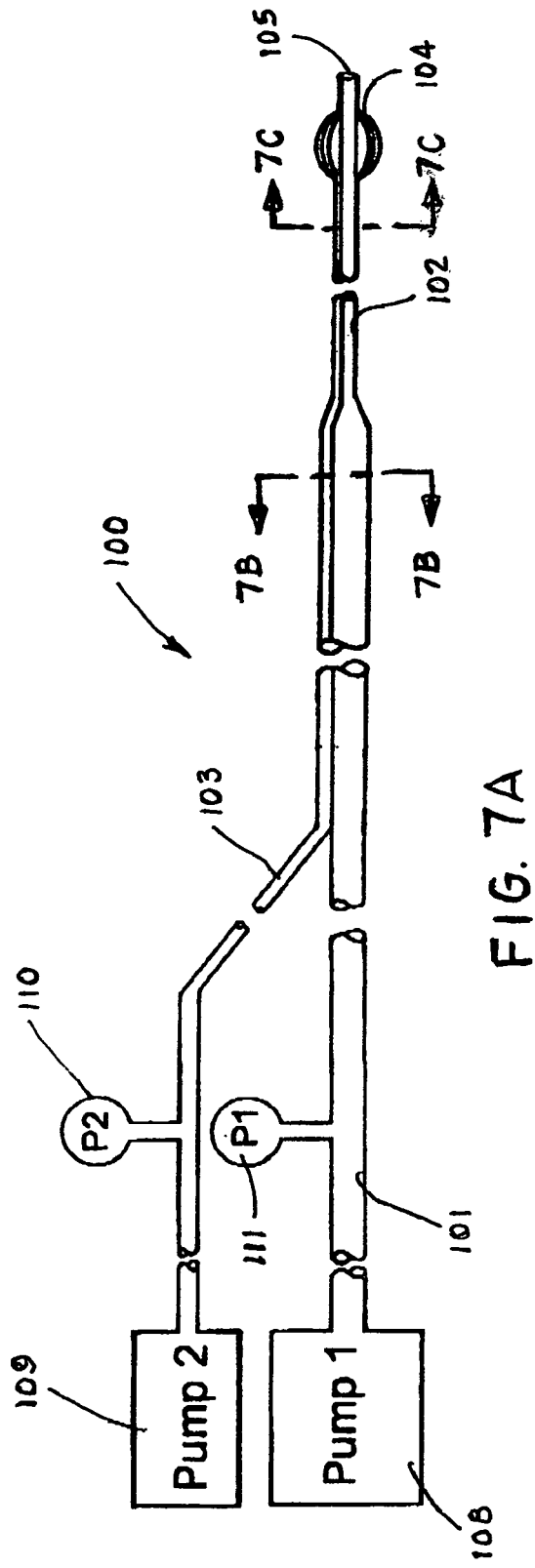
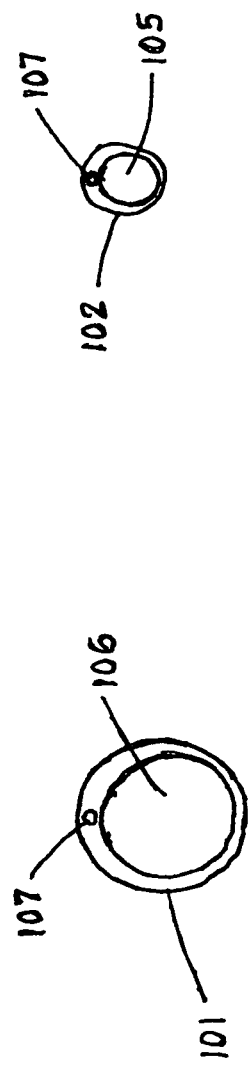
FIG. 7A
FIG. 7B
FIG. 7C

METHOD FOR CONTROL OF STEM CELL INJECTION INTO THE BODY

CROSS-REFERENCE TO RELATED APPLICATION

This application is a continuation-in-part of Ser. No. 10/955,403, filed Sep. 30, 2004, which is a continuation-in-part of U.S. Pat. No. 6,805,860 (having matured from Ser. No. 09/968,739, filed Sep. 30, 2001) of the same applicant. Applicant claims priority of the '403 application with respect to common subject matter. The '403 application is incorporated by reference herein, although certain portions are duplicated herein for convenience to the reader.

BACKGROUND OF THE INVENTION

The present invention relates generally to transluminal application of therapeutic cells for tissue repair, such as myocardial repair, and more particularly to balloon catheter protected transluminal application of multipotent (stem) cells for repair of a failing body organ such as heart, brain, liver, kidney or pancreas, and even related glands, nerves, and muscles. More specifically, the invention provides a novel method to repair failing tissue, and, in conjunction therewith, instrumentation and a method for the control of stem cell injection into the body.

The present invention involves considering parameters that determine conditions for injecting stem cells into a distinct area of the human body, and provides a method to achieve an adapted and titrated treatment form with respect to the various locations of stem cell injection, and also with respect to the different properties of the injected stem cells and the respective organ targeted for repair in an individual patient.

In principle, the human body has three types of cells: (1) cells that continuously undergo replication and reproduction, such as dermal cells and epithelial cells of the intestine, which have a life as short as ten days and are replaced by the same cell type in replication; (2) cells differentiated in the adult state, but having the potential to undergo replication and the ability to reenter the cell cycle under certain conditions, such as liver cells, which enable the liver to regrow and repair itself even if a major portion of the liver is removed; and (3) cells that stop dividing after they have reached their adult stage, such as neuro cells and myocardial cells.

For the latter type or group of cells, the number of cells in the body is determined shortly after birth. For example, myocardial cells stop dividing at about the 10th day after delivery, and a fixed number of myocardial cells remains for the rest of the human body's life. Changes in myocardial function occur not by division and new cell growth, but only as a result of hypertrophy of the cells.

Although the absence of cell division in myocardial cells is beneficial to prevent the occurrence of tumors—which practically never occur in the heart—it is detrimental to local repair capacities. During the individual's lifetime, myocardial cells are subjected to various causes of damage, which irreversibly lead to cell necrosis or apoptosis.

The primary reason for cell death in the myocardium is ischemic heart disease—in which the blood supply to the constantly beating heart is compromised through either arteriosclerotic build-up or acute occlusion of a vessel following a thrombus formation, generally characterized as myocardial infarction (MI). The ischemic tolerance of myocardial cells following the shut-off of the blood supply is in a range of three to six hours. After this time the overwhelming majority of cells undergoes cell death and is replaced by scar tissue.

Myocardial ischemia or infarction leads to irreversible loss of functional cardiac tissue with possible deterioration of pump function and death of the individual. It remains the leading cause of death in civilized countries. Occlusion of a coronary vessel leads to interruption of the blood supply of the dependent capillary system. After some 3 to 6 hours without nutrition and oxygen, cardiomyocytes die and undergo necrosis. An inflammation of the surrounding tissue occurs with invasion of inflammatory cells and phagocytosis of cell debris. A fibrotic scarring occurs, and the former contribution of this part of the heart to the contractile force is lost. The only way for the cardiac muscle to compensate for this kind of tissue loss is hypertrophy of the remaining cardiomyocytes (accumulation of cellular protein and contractile elements inside the cell), since the ability to replace dead heart tissue by means of hyperplasia (cell division of cardiomyocytes with formation of new cells) is lost shortly after the birth of mammals.

Other means of myocardial cell alteration are the so-called cardiomyopathies, which represent various different influences of damage to myocardial cells. Endocrine, metabolic (alcohol) or infectious (virus myocarditis) agents lead to cell death, with a consequently reduced myocardial function. The group of patients that suffer myocardial damage following cytostatic treatment for cancers such as breast or gastrointestinal or bone marrow cancers is increasing as well, attributable to cell necrosis and apoptosis from the cytostatic agents.

Prior to advances described in applicant's '860 patent and '403 application, the only means for repair has been to provide an optimal perfusion through the coronary arteries using either interventional cardiology—such as PTCA (percutaneous transluminal coronary angioplasty), balloon angioplasty or stent implantation—or surgical revascularization with bypass operation. Stunned and hibernating myocardial cells, i.e., cells that survive on a low energy level but are not contributing to the myocardial pumping function, may recover. But for cells that are already dead, there has been no recovery.

The current state of interventional cardiology is one of high standard. Progress in balloon material, guide wires, guiding catheters and the interventional cardiologist's experience as well as the use of concomitant medication such as inhibition of platelet function, has greatly improved the everyday practice of cardiology. But an acute MI remains an event that, even with optimal treatment today, leads to a loss of from 25 to 100% of the area at risk—i.e., the myocardium dependent on blood supply via the vessel that is blocked by an acute thrombus formation. Complete re-canalization by interventional means is feasible, but the ischemic tolerance of the myocardium is the limiting factor.

An article published in 2000 (Schömig A. et al., "Coronary stenting plus platelet glycoprotein IIb/IIIa blockade compared with tissue plasminogen activator in acute myocardial infarction," N Engl J Med 2000; 343:385-391), reports on a study, for which the applicant herein was a clinical investigator, of the myocardial salvage following re-canalization in patients with an acute MI. The average time until admission to the hospital was 2.5 hours and complete re-canalization was feasible after 215 minutes, about 3.5 hours. Still, only 57% of the myocardium at risk could be salvaged by re-canalization through interventional cardiology by means of a balloon and stent. When the group of patients was randomized to classical thrombolytic therapy—the worldwide standard (no interventional means)—only 26% of the myocardium at risk could be salvaged. Thus, even under optimal circumstances more than 40% of the myocardial cells are irreversibly lost. Many patients arrive at hospital 6-72 hours after acute symptoms of vessel blockage by a thrombus, so the average loss of affected myocardial tissue is assumed to range from 75-90% after acute MI.

Cells can survive on a lower energy level, referred to as hibernating and stunning myocardium, so as collateral blood flow increases or re-canalization provides new blood supply they can recover their contractile function. The principle of myocardial reperfusion, limitation of infarct size, reduction of left ventricular dysfunction and their effect on survival are described by Braunwald et al. in "Myocardial reperfusion, limitation of infarct size, reduction of left ventricular dysfunction, and improved survival: should the paradigm be expanded?," *Circulation* 1989; 79:441-4.

Annually, about five million Americans survive an acute MI. Clearly then, loss of affected myocardial tissue is a problem of major clinical importance. Currently, repair is limited to hypertrophy of the remaining myocardium, and optimal medical treatment by a reduction in pre- and after-load as well as the optimal treatment of the ischemic balance by β-blockers, nitrates, calcium antagonist, and ACE inhibitors.

Replacement of the dead myocardium (scar tissue) by re-growing cells is expected to have a profound impact on the quality of life of affected patients.

In addition to ischemic heart disease, among other causes for the reduction of myocardial cells that contribute to pumping or electrical function of the heart are the cardiomyopathies, which describe a certain dysfunction of the heart. Reasons include chronic hypertension that ultimately leads to a loss in effective pumping cells, and chronic toxic noxious such as alcohol abuse or myocarditis primarily following a viral infection. Also, cell damage in conjunction with cytostatic drug treatment is becoming of greater clinical relevance. The contracting myocardium becomes affected, as well as the conduction system of the heart. Clinical symptoms are slow or fast heart rates, generally called sinus node disease, AV Block conduction block and re-entry tachycardias and atrial flutter, atrial fibrillation, ventricular tachycardias and ventricular fibrillation.

In their initial report (Goldstein M. A. et al., "DNA synthesis and mitosis in well-differentiated mammalian cardiocytes," *Science* 1974; 183:212-3), the group of William C. Claycomb et al., which has engaged in research on the behavior and development of myocytes since the early 1970's, described the incorporation of 3H-Thymidin into the nuclei of heart cells of two days old rats which indicates that neonatal cardiac cells still undergo synthesis of DNA and divide despite the presence of contractile proteins. This phenomenon of cell division ceases at day 17 of the postnatal development. After that time no further division of cardiac cells occurs, either in rats or in humans.

The interest in mammalian cardiomyocytes has led to the development of cultures of adult cardiac muscle cells (Claycomb W. C. et al., "Culture of the terminally differentiated adult cardiac muscle cell: A light and scanning electron microscope study," *Dev Biol* 1980; 80:466-482), and ultimately to the generation of a transplantable cardiac tumor-derived transgenic AT1-cell.

During the 1980's studies were conducted with the characterization of this atrial derived myocyte cell line, which is immortalized by the introduction of the SV40-large-T-oncogene (SV40-T). From this AT-1-cell-group, other adult cardiomyocytes have been derived, described as HL-1-cells, which can be passaged indefinitely in culture, recovered from a frozen stock, retain a differentiated cardiomyocyte phenotype, and maintain their contractile activity. Among the references are Delcarpio J. B. et al., "Morphological characterization of cardiomyocytes isolated from a trans-plantable cardiac tumor derived from transgenic mouse atria (AT-1 cells)," *Circ Res* 1991; 69(6):1591-1600; Lanson Jr. N. A. et al., "Gene expression and atrial natriuretic factor processing and secretion in cultured AT-1 cardiac myocytes," *Circulation* 1992; 85(5):1835-1841; Kline R. P. et al., "Spontaneous activity in transgenic mouse heart: Comparison of primary atrial tumor with cultured AT-1 atrial myocytes," *J Cardiovasc Electrophysiol* 1993; 4 (6):642-660; Borisov A. B. et al., "Proliferative potential and differentiated characteristics of cultured cardiac muscle cells expressing the SV 40 T oncogene," *Card Growth Reg* 1995; 752:80-91; and Claycomb W. C. et al., "HL-1 cells: A cardiac muscle cell line that contracts and retains phenotypic characteristics of the adult cardiomyocyte," *Proc Natl Acad Sci USA* 1998; 95:2979-84.

Cardiomyocyte transplantation in a porcine MI model has been studied intensively in collaboration with the research group of Frank Smart (Watanabe E. et al., "Cardiomyocyte transplantation in a porcine myocardial infarction model," *Cell Transplant* 1998; 7(3):239-246). In conjunction with AT-1 cardiomyocytes, human fetal cardiomyocytes were injected through a syringe and needle into the adult pig heart infarction area.

In summary, these cells showed local growth and survived in the infarction border zone, but could not be found in the core scar tissue of the myocardial infarction. The majority of the implanted cells were replaced with inflammatory cells, suggesting that the immuno-suppressant regimen that was concomitantly applied was not sufficient for the grafted cells to survive in the host myocardium. Other factors that may have influenced the result that the transplanted cells were not detected, could possibly be linked to the fact that the cells were grafted 45 days after inducing the infarction.

It is known that the inflammatory stimuli for cell growth are significantly reduced in the first two to three weeks of an MI. Also, that transforming-growth-factor-b (TGF-b), fibroblast-growth-factor-2 (FGF-2), platelet-derived-growth-factor (PDGF) and other cytokines, like the interleucin-family, tumor-necrosis-factor-a (TNF-a) and interferon-gamma are strong stimulators of cell proliferation and cell growth. The adjunct therapy with immuno-suppression has further reduced these stimuli for cell growth.

Another major factor for the failure of detection of grafted cells in the myocardial scar may be the selection of the infarction model. An artery is occluded and the blood supply has not recovered before grafting. There is no reason to assume that the grafted cells could survive in an ischemic area and grow, better than the myocytes.

Therefore, other groups have tried to induce a myocardial angiogenesis by gene-therapy. This was either performed by the administration by fibroblast growth factor II in the presence or absence of heparin (see Watanabe E. et al., "Effect of basic fibroblast growth factor on angiogenesis in the infarcted porcine heart," Basic Res Cardiol 1998; 93:30-7) or by application of vascular endothelial growth factor (VEGF), a potent mitogen for endothelial cells. VEGF stimulates capillary formation and increases vascular permeability (Lee J. S. et al., "Gene therapy for therapeutic myocardial angiogenesis: A promising synthesis of two emerging technologies," *Nat Med* 1998; 4 (6):739-42). Still other groups have tried to increase the collateral capillary blood flow by human bone marrow derived angioblasts and have shown an improvement in acute myocardial infarction in rats treated with injections of colony-stimulating-factor-G (CSF-G) mobilized adult human CD-34 cells (Kocher A. A. et al., "Neovascularization of ischemic myocardium by human bone-marrow-derived angioblasts prevents cardiomyocyte apoptosis, reduces remodeling and improves cardiac function," *Nat Med* 2001; 7 (4):430-6).

While these approaches certainly have some research merit, their clinical relevance for the majority of patients is not as important, since we have effective means to re-canalize an occluded vessel and provide a blood supply via the natural branching of the coronary arteries, which further subdivides into arterioles and capillaries.

Other attempts to transplant preformed patches also necessitate the growth of the grafted cells in a patch formation and a surgical operation in a patient, which requires opening the thoracic cage.

Considering the complications, the cost and the risk associated with these time consuming procedures, it becomes clear that they offer only limited likelihood for widespread routine application.

Other groups have tried to make use of the precursor cells that are found in the peripheral muscle. Unlike the heart, there is a certain degree of repair in peripheral skeletal muscles, since the peripheral skeletal muscle contains progenitor cells, which have the capability to divide and replace the peripheral muscle. By isolating those cells from a probe of a thigh muscle, the progenitor cells of skeletal muscle have been separated, cultured and re-injected in an animal model (Taylor D. A. et al., "Regenerating functional myocardium: Improved performance after skeletal myoblast transplantation," *Nat Med* 1998; 4 (8):929-33; Scorsin M. et al., "Comparison of the effects of fetal cardiomyocyte and skeletal myoblast transplantation on postinfarction left ventricular function," *J Thorac Cardiovasc Surg* 2000; 119:1169-75), and more recently in some patients also.

The application of these cultured cells has also been attempted by injection with small needles following an opening of the subject's chest and the pericardial sac. While in the model of kryo-infarction, in which only the myocardial cells die but the blood supply through the vascular system is not limited, the injection of autologous skeletal myoblasts improves the myocardial function. The results indicated, however, that the engrafted cells retain skeletal muscle characteristic, which means they cannot contract at the constant fast rate imposed by the surrounding cardiac tissue. In addition, no electrical connection exists between the graft cells and the host tissue, and it is assumed that their contribution to improve contractile performance probably resulted from the mechanical ability of the engrafted contractile tissue to respond to stretch activation by contraction.

Considering the experience with latissimus dorsi muscle grafting—a procedure called dynamic cardiomyoblasty—, disappointing results with the possible use of skeletal muscle as a myocardial substitute indicate that the long term different muscle characteristics of skeletal muscles do not match the need of a constantly pumping myocardial cell. Therefore, these cells might achieve at best improving the quality of the scar of the ischemic myocardium, but not actively contributing long term to a contraction of this area.

The disclosure of the '403 application is directed to interventional medicine through an intraluminal application of cells that have the capability to replace the necrotic tissue of a failing organ, such as the heart in the case of a MI, to resume the myocardial function and therefore improve the pumping performance of the myocardium.

The procedure is oriented on the clinical practice of interventional cardiology following the principle that only those approaches that are both (a) relatively easy to perform, with little or no risk to the patient but a potentially high benefit, and (b) highly cost effective, are likely to be routinely applied in everyday medicine.

An important aspect of the invention described in the '403 application is that the cells to be used in the intraluminal or transluminal application preferably are autologous adult stem cells, which are derived from the same patient that has suffered the infarction. The cells are harvested and separated before injection, from the same individual (autologous transplantation). In a case of failing tissue of the myocardium, these cells are then injected into the coronary artery that caused the infarction or into the corresponding coronary vein in a retrograde manner.

The approach taken there recognizes the need to give stem cells a certain contact time to adhere and migrate from the vascular bed into the infarcted myocardial area. In contrast to previous approaches, in which patches or applications through needles into the infarcted area have been considered, the inventive approach hypothesizes that the most effective way to deliver the cells to the infarcted area is through the vascular tree of coronary arteries, arterioles and capillaries that supply the infarcted area. An occlusion balloon of an over the wire type catheter is inflated at the site of the primary infarction, after the vessel has been re-canalized and the blood flow reconstituted.

While the blood flow is still blocked, the stem cells are supplied by slow application through the balloon catheter over a relatively short period of time, 10 to 15 minutes, for example. That is, the stem cells are injected through the inner lumen of the catheter while the balloon is inflated, and therefore, no washout occurs. This intracoronary, intravascular, intraluminal, or transcoronary application of cells during a period that flow or perfusion is ceased is believed to be critical to enabling the cells to successfully attach to the myocardial wall. And further, to overcome more actively the endothelial barrier following the increased pressure in the vascular bed or duct, which is attributable to the retrograde flow of cells being limited through the inflated balloon catheter.

These principles of that invention are not limited to cellular repair of damaged or failing myocardial tissue, but may be applied in processes for repair of tissue of various organs of the body, additionally including the brain, liver, kidney, pancreas, lungs, related glands, nerves, and muscles, for example, by intraluminal application of the stem cells through an appropriately designated vessel or duct leading to the targeted tissue.

Thus, according to the invention of the '403 application, a method for repairing tissue of an organ in a patient's body includes delivering adult stem cells that have the capability to replace tissue of a failing organ to the site of the tissue to be repaired, by an intraluminal application through a blood vessel of or duct to the site, and occluding the blood vessel or duct proximal to the location of cell entry therein via the intraluminal application during at least a portion of the duration of the cell delivery to increase the concentration of cells delivered to the site. A balloon catheter is preferred for the intraluminal application, and the occlusion is performed by inflating the balloon of the catheter for a time interval prescribed to increase the concentration of cells delivered to the site. Initially, a guide wire is introduced through the vessel or duct to the site, to allow the catheter to be advanced over the wire until the distal end reaches the vicinity of the target site for delivery of the stem cells.

The autologous adult cells utilized for that method may be harvested from the patient's own body, such as from the bone marrow, adipose tissue, or may originate from lipoaspirate. Harvesting should be within a short time interval immediately prior to delivery of the cells to the organ site to enhance the likelihood of successful organ repair.

It had been hypothesized by most researchers that adult stem cells are tissue specific and that a certain stem cell-like population exists in every organ and is capable of differentiation into this certain tissue with exceptions to this rule regarding repair in heart and brain. Studies reported in and after the year 2000 indicated an underestimated potential of these cells. It was shown that murine and human neural stem cells (NSC) give rise to skeletal muscle after local injection (see, for example, Galli R et al., "Skeletal myogenic potential of human and mouse neural stem cells," *Nat Neurosci* 2000;3: 986-991). Bone marrow stem cells have were shown to replace heart tissue (cardiomyocytes, endothelium and vascular smooth muscle cells) after injection into lethally irradiated mice with a myocardial infarction (see Jackson K. A. et al., "Regeneration of ischemic cardiac muscle and vascular endothelium by adult stem cells," *J Clin Invest* 2001;107(11): 11395-402). The tissue damage in general appears to transmit signals which direct multi-potential stem cells to the site of destruction, and these precursors undergo a multi-step process of migration and differentiation at the organ site to replace damaged cells in form and function.

Experiments with cultured fetal cardiac myocytes or neonatal myocytes impose limitations owing to their heterologous nature and their possible induction of an immuno response necessitating an immuno-suppressive therapy. Complications and risks associated with an immuno-suppressant therapy are an increased susceptibility to infection and the possible development of malignancies. In addition, it was speculated that only a few patients would be willing to undergo a long term immuno-suppressive therapy with all its negative side effects.

An alternative approach by Prockop suggested that marrow stromal cells act as stem cells for non hematopoetic tissue, capable to differentiate into various types of cells including bone, muscle, fat, hyaline cartilage and myocytes (Prockop D. J. et al., "Marrow stromal cells for non hematopoetic stem tissues," *Science* 1997; 276:71-74).

Findings reported since 2000 piqued interest in adult cardiomyocytes. A report in Nature describes the ability to inject adult bone marrow stem cells from transgenic mice into the border of infarcted myocardial tissue (Orlic D. et al., "Bone marrow cells regenerate infarcted myocardium," *Nature* 2001; 410:701-5). According to this report, these adult stem cells are capable of differentiation into cardiomyoblasts, smooth muscle cells and endothelial cells after injection. The infarcted myocardium implied that the transplanted cells responded to signals from the injured myocardium which promoted their migration, proliferation and differentiation within the necrotic area of the ventricular wall.

The classical way to recover adult stem cells is a bone marrow tap. The bone marrow contains a wide variety of hematopoetic and mesenchymal stem cells in addition to the T-lymphocytes, macrophages, granulocytes and erythrocytes. By incubation with monoclonal antibodies specific for the respective cell lineages and by sorting and removing with a biomagnet after incubation with magnetic beads and cell sorting with FACS (fluoroscopy activated cell sorting), a highly enriched cell line of bone marrow derived stem cells can be insulated, cultured and grown.

A subsequent report indicated that cells from human adipose tissue contain a large degree of mesenchymal stem cells capable of differentiating into different tissues in the presence of lineage specific induction factors including differentiation into myogenic cells (see Zuk P. A. et al., "Multilineage cells from human adipose tissue: Implications for cell-based therapies," *Tiss Engin* 2001; 7(2):211-28). The interesting approach in this research was that out of a lipoaspirate of 300 $cm^3$ from the subcutaneous tissue, an average of $2-6 \times 10^8$ cells can be recovered. Even if one assumed that after processing of this liposuction tissue and separation and isolation of the mesenchymal stem cells, only 10% of these stem cells might be left for culture, the remaining approximately $10^7$ (10 million) cells would be quite sufficient to be used for the intraluminal or transluminal transplantation process.

The latter approach appeared to benefit by avoiding culture and passaging of the stem cells. This is important, since in the early phases of MI high activity of inflammatory cytokines promote adhesion, migration and proliferation of the stem cells. In addition, as long as no scar core tissue is formed it is much easier for these cells to migrate into the whole area of myocardial infarction and resume the cardiac function.

More recently, embryonic stem cells became the subject of intensive discussion, particularly their pluripotency to differentiate into a vast range of tissues and organs of the human body that are in need for repair. The discussion has included the potential use of such stem cells for replacement of insulin producing cells as well as embryonic stem cells that can differentiate into cells with structural and functional properties of cardiomyocytes. See, for example, Kehat I. et al., "Human embryonic stem cells can differentiate into myocytes with structural and functional properties of cardiomyocytes," *J Clin Invest* 2001; 108:407-14. Earlier, the proliferation of embryonic stem cells was elegantly described in principle in Klug M. G. et al., "Genetically selected cardiomyocytes from differentiating embryonic stem cells form stable intracardiac grafts," *J Clin Invest* 1996; 98(1):216-24. The latter group succeeded in plating a cell line following a fusion gene consisting of the a—cardiac-myocyte-heavy-chain-promotor and the c-DNA encoding aminoglycoside-phosphotransferase that was stably transfected into pluripotent embryonic stem cells. The resulting cell lines were differentiated in vitro and subjected to a G418 selection. The selected cardiomyocyte cultures were 99.6% pure and highly differentiated.

It is important to consider the engraftment of pluripotent embryonic stem cells into a failing organ, but also the possibility of resulting tumor formation. Therefore, pluripotent embryonic stem cells need to be cultured in an undifferentiated status, transfected via electroporation and grown in differentiated cultures. The interesting approach in this work is the high yield of selected embryonic stem cell derived cardiomyocytes which, with simple genetic manipulation, can be used to produce pure cultures of cardiomyocytes. It has also been reported that isolation of primate embryonic stem cells with cardiogenic differentiation is feasible (Thomson J. A. et al., "Isolation of a primate embryonic stem cell," *Proc Natl. Acad Sci USA* 1995; 92:7844-48).

In addition, it was reported that human cardiomyocytes can be generated from marrow stromal cells in vitro as well, but with a low yield of differentiated myocytes (Makino S. et al., "Cardiomyocytes can be generated from marrow stromal cells in vitro," *J Clin Invest* 1999; 103:697-705). The 1997 Prockop report (supra) in Science describes another line of cardiomyocytes generated from marrow stromal cells in vitro. This cardiomyogenic cell line was derived from murine bone marrow stromal cells that were immortalized and treated with 5-azacytidine. By mechanically separating spontaneously beating cells, a cell line was isolated that resembled a structure of fetal ventricular cardiomyocytes expressing isoforms of contractile protein genes such as alpha cardiomyocyte heavy chain, -light chain, a-actin, Nkx2.5-Csx, GATA-4, tef-1, MEF-2a and MEF-2D.

While these embryonic stem cells provide optimism for the future that cardiomyocytes derived from embryonic cells might fulfill the requirements of cells that can (a) be passaged indefinitely in culture, (b) be recovered from frozen stocks and are readily available if a patient with a myocardial infarction comes to the cath lab, (c) retain their differentiated cardiomyocyte phenotype and (d) maintain contractile activity with minimum or no immunogenity, further basic research is needed before they can be applied in the animal model. It is likely that a primate model of infarction and the transplantation of primate embryonic stem cell derived cardiomyocytes may be needed as the final proof of principle before a human study might be conducted.

For ethical, immunological and feasibility reasons, the applicant's 403 application proposed transplantation of autologous adult stem cells to be the most straightforward and practical approach to repair failing myocardium. The process of that application promotes invasion of ischemically injured cardiac tissue by stem cells that firmly attach and subsequently undergo differentiation into beating cardiomyocytes that are mechanically and electrically linked to adjacent healthy host myocardium. Adhesion of the injected stem cells and their migration beyond the endothelial barrier may be confirmed by observation after several days of frozen sections using light microscopy and, subsequently, electron microscopy. For evidence of the transition of stem cells into cardiomyocytes, markers are introduced into the stem cells before they are re-injected into the myocardial tissue to be repaired.

One proposal was to transplant male cells carrying the Y-chromosome into a female organism, but at least two factors weigh against this. It could lead to immunologic problems because of the different cell surfaces carried by the recipient and the donor (heterologous transplant), a potential reason that some studies are not able to show a successful heterologous cell transplantation. More importantly, a predominance of inflammatory cells exists at the site of myocardial injury, which leads to an immediate recognition of foreign cell surface proteins with consequent elimination of the cells. Use of autologous stem cells would not carry this immunologic risk of cell destruction, although some difficulty is encountered in prior introduction of genetic or protein markers into those cells.

To overcome this difficulty, a green fluorescence protein (GFP) was used as a marker, with introduction into the stem cell genome by liposomal gene transfer. Cells can then be identified after transplantation by fluorescence microscopy. As part of the procedure, stem cells are also marked by 3H-Thymidin, a radioactive labeled part of DNA. All stem cells undergoing DNA replication for mitosis will introduce 3H-Thymidin into their genome, and thus can be detected afterwards by gamma count. One limitation of this process is the fact that radioactivity (per volume) declines with each subsequent cell division (albeit initial total radioactivity stays constant). Nevertheless, this marker aids in developing a gross estimate of the amount of cells in a certain organ or tissue (e.g., heart, spleen, liver etc.).

Referring to FIG. 1, taken from the '403 application, subcutaneous adipose tissue 20 is obtained from a liposuction procedure on a patient 1 during local anesthesia. A hollow canule 21 is introduced into the subcutaneous space through a small cut. Gentle suction by a syringe 22 as the canule is moved through the adipose compartment mechanically disrupts fat tissue. Following a normal saline solution and a vasoconstrictor epinephrine, a lipoaspirate of 300 cc. is recovered within the syringe, and is processed immediately to obtain a high density cellular pellet. Following filtration to remove cellular debris, the cells are ready to be injected into the area of interest in the patient's body.

Referring to FIG. 2, also from the '403 application, as well as to FIG. 1, the recovered autologous adult stem cells are transplanted in the donor patient by intracoronary or transcoronary application for myocardial repair. A balloon catheter 11 is introduced into the cardiovascular system at the patient's groin 3 using an introducer 4, and through a guiding catheter 5 over a guide wire 18 into the aorta 6 and the orifice 7 of a coronary artery 8 of the heart 2 at or in the vicinity of the site where failed tissue, e.g., from an infarction, is to be repaired. The failed tissue is supplied with blood through artery 8 and its distal branches 9 and 10. The cells are hand injected or injected through the inner lumen 12 of the balloon catheter 11 by a motor driven constant speed injection syringe 16 and connecting catheter 17 to an entry point of the central lumen at the proximal end of catheter 11. The exit point of the central lumen 12 is at the distal end of catheter 11 which has been advanced into the coronary artery 8 in proximity to the site of the desired repair. The cells 15 are delivered to this site by means of slow infusion over 15-30 minutes, for example.

Normally anything inside the blood vessel, including these cells, is separated from the parenchymatous organ or the tissue outside the vessel. Blood flows through the larger arteries into the smaller arteries, into the arterials, into the capillaries, and then into the venous system back into the systemic circulation. Normally, the cells would be prevented from contacting the tissue to be repaired because of the endothelial lining and layer of the vessel that protects the tissue. But under certain circumstances this barrier is overcome, and the cells can attach to the inside of the vessel, migrate and proliferate in the adjacent tissue. These circumstances are facilitated in the case of situations of acute inflammation such as an acute myocardial infarction, and the increased pressure in the injection system promotes the injected cells to overcome the barrier.

The endothelial ischemic damage owing to the infarction allows white blood cells, especially granulocytes and macrophages, to attach via integrins to the endothelial layer. The endothelial layer itself is dissolved in places by release of hydrogen peroxide ($H_2O_2$) which originates from the granulocytes. This mechanism produces gaps in the endothelial layer that allow the stem cells to dock to the endothelial integrins and also to migrate through these gaps into the tissue to be repaired. An adjacent factor that enables the stem cells to migrate into the organ tissue is referred to as a stem cell factor that acts as a chemo-attractant to the cells.

A sufficient quantity of the repair cells must be allowed to migrate into contact with the failing tissue to achieve a high number of transplanted cells in the tissue. This is the principal reason for using a balloon catheter 11 or some other mechanism that will allow the physician to selectively block the antegrade blood flow and the retrograde stem cell flow. In the process, the balloon 14 of catheter 11 is inflated with biocompatible fluid through a separate lumen 13 of catheter 11 to occlude coronary artery 8 and its distal branches 9 and 10, thereby causing perfusion through the vessel to cease. The balloon is inflated immediately before or upon injection of the stem cells through the inner lumen of the catheter, and maintained throughout the period of injection. This enables the desired large number of adhesions of the cells 15 to the failing tissue to be achieved. The absence of blood flow at the critical site of this tissue to be repaired prevents what would otherwise result in a retrograde loss of injected cells, an inability to increase the pressure at the injection site to overcome the endothelial barrier and to force the cells through the gap, and an antegrade dilution with blood flow of the cells being injected to that location through the catheter 11.

Depending on the type and number of cells delivered, the blockage is maintained for a relatively short period of time, e.g., on the order of 1-15 minutes, sufficient to allow a high concentration and considerable number of cell attachments to the tissue at the designated site, to achieve a successful repair. The balloon is deflated, and the balloon catheter is removed from the patient following the designated period.

The invention of the '403 application uses the natural distribution tree of the arterioles and the capillaries, provided that the transplanted cells can overcome the endothelial barrier and migrate into the tissue, and interventional cardiology means can restore blood flow into the infarcted area again.

In clinical practice there is a 96% success rate with interventional cardiology to restore blood flow following an acute MI after an occlusion of a coronary artery. Since venously injected stem cells can be found in the myocardium, and in an acute MI the endothelial barrier is considerably damaged, it may be concluded that a local injection into the infarcted area with an occlusive balloon to prevent a washout of the cells is a highly desirable approach. In studies performed in the past with a technique called 'BOILER'-lysis, older venous bypass grafts were occluded by a thrombus that has grown over a prolonged period of time, and it was observed that an acute injection of a thrombolytic agent rarely dissolved these old thrombi. But after an over the wire balloon catheter was inserted into the occluded graft, a prolonged application of a thrombolytic substance such as urokinase was successful in achieving thrombolysis. The agent is injected at the tip of the balloon catheter, and is forced antegradely into the thrombus. The inflated balloon prevents a washout by the normal coronary circulation and allows the injection at a defined volume per time.

The process of the '403 application may be applied to the brain in the case of a patient having suffered a cerebral damage such as an infarction. Previous studies indicated that stem cells have the capacity to replace neural cells in the brain and overturn the consequences of an acute vascular stroke. The injection catheter would be advanced to the site of the damaged tissue through an appropriate arterial path into the applicable region of the patient's brain. Blockage of blood flow in this case would add a period (e.g., minutes) of limited blood supply but would enable the cells to overcome the endothelial barrier.

Other body organs having damaged tissue to be repaired by variations of this process include the pancreas, the liver, and the kidneys. The pancreas has a duct (the ductus Wirsungii) through which pancreatic enzymes are delivered into the intestines, and which can be accessed in a retrograde manner by endoscopic retrograde choledocho-pancreaticography (ERCP). Failing tissue in the case of a diabetic patient means that the pancreatic cells therein no longer produce sufficient insulin for the patient's needs. By visual guidance through a small fiberglass instrument a small balloon catheter is introduced into this duct, and the balloon inflated to occlude the duct during delivery of stem cells through the catheter to the site of the damaged tissue, so as to prevent the injected cells from being washed out into the intestines, to enhance large scale adhesions and penetration of the cells to the target tissue.

An analogous procedure is used for repair of damaged tissue of the liver, through the bile duct system. The normal bile duct barrier is overcome with pressure that can be generated if the balloon is inflated while the cells are slowly injected. The pressure distally of the injection site increases as more and more cells are injected. Repair of failing tissue in the kidney(s) from renal infarction is achieved by an analogous procedure.

The '403 application also describes a process to open up the blood circulation in an ischemic organ and, to inject stem cells for repair of tissue damage in the organ occasioned by prior blockage. In a myocardial infarction, for example, only a portion of the myocardial cells that had been ischemic will survive. A typical procedure is to perform a balloon angioplasty of the blocked artery, followed by implanting a stent at the site of the lesion. But even in the case of optimal treatment some 40% of the affected cells will die. To reduce this effect, autologous adult stem cells are injected into the organ proximate the site of the target tissue for repair thereof within a predetermined brief period after opening the ischemic organ to circulation of blood flow.

Referring to FIG. 3, also taken from the '403 application, in a method for delivery of stem cells through a balloon catheter to the anterior cerebral circulation in a patient 31, an introducer sheath 33 is advanced through the right groin 32, and a balloon double lumen catheter 34 is advanced through introducer sheath 33 and over a guide wire 48 placed in the artery of interest. The proximal end of guide wire 48 is left to project from opening 35a of catheter 34. A side branch opening 35b of catheter 34 is operatively coupled through an inflation lumen of the catheter for selective inflation and deflation of its balloon 46.

Guide wire 48 is advanced through the central lumen of catheter 34, and the catheter is then maneuvered to the selected site over the guide wire through iliac artery 37, abdominal and thoracic aorta 38, aortic arch 39, and into the right carotid artery 40 beyond the branching of the vessels 41 for the right arm. Alternatively, the guide wire and catheter are advanced to a location in the left carotid artery 42, which either originates after the branch-off of the left subclavian artery 43, or directly from the aortic arch 39 where the left subclavian artery originates from a separate orifice.

The guide wire is advanced through the common carotid artery into the right internal carotid artery 40 and into the proximal circulation of the Circulus Willisi 44, to encounter the anterior cerebral artery 45 at its origination. Catheter 34 is then advanced to position its tip 47 and balloon 46 in the anterior cerebral artery 45, with the catheter tip located at the site for delivery of the harvested autologous adult stem cells, and guide wire 48 is removed. The opening 35a of the same lumen used for the guide wire is now available for injecting stem cells for delivery to that site.

Referring also to FIGS. 3A and 3B, the conus 50 of a syringe 49 (FIG. 3A) is connected to port 35a of catheter 34, and the conus 53 of another syringe 52 (FIG. 3B) is connected to the inflation port 35b of catheter 34. Port 35b operates through the inflation lumen for balloon 46 of catheter 34. Syringe 52 is of small size and includes a pressure gauge 55 to measure the applied pressure as the fluid 54 within the syringe is expelled into port 35b to inflate balloon 46 to a low pressure of 0.5 to 0.8 atm. This pressure is sufficient to tightly seal the vessel (anterior cerebral artery 45) at the location of the balloon. To assist in recognizing a possible rupture of balloon 46, the fluid 54 in syringe 52 is a 50/50 mixture of saline and contrast dye. Balloon 46 may be deflated on completion of the procedure or in an emergency by withdrawing the fluid 54 back into syringe 52.

While anterior cerebral artery 45 is tightly sealed toward its proximal end 44, stem cells 51 within syringe 49 are slowly ejected from conus 50 into port 35a of the catheter. The stem cells travel through the central lumen of catheter 34 formerly occupied by guide wire 48 and exit the lumen at the site of catheter tip 47. The stem cells thus enter into the cerebral circulation at that site. The very brief period of limited blood supply during blockage of blood flow through artery 45 by inflated balloon 46 is sufficient for the stem cells to overcome the endothelial barrier but not enough to cause injury to the brain.

For treating a diseased kidney, stem cells are introduced similarly through a catheter navigated over a guide wire in the patient's right groin into the iliac artery 37, the abdominal aorta 38, the applicable renal artery 57, and the diseased kidney 58.

FIG. 4, also taken from the '403 application, illustrates a method for delivery of stem cells through a natural duct in a patient 61. In this procedure, an endoscope 64 is advanced through the mouth 62 and esophagus 63 of the patient. The endoscope 64 is flexible, and designed and implemented with a plurality of channels including a visualization and fiber optics channel 65, flushing channel 66, side port open channel 67, and working channel 68. The distal tip 75 of endoscope 64 is readily bendable to allow it to be advanced through a tortuous path. The endoscope 64 is advanced from the esophagus 63 through the diaphragm 70, through the stomach 69, and until its distal tip is located in the duodenum 71.

If the pancreas is to be repaired, the distal tip is positioned such that a side port 72 of the endoscope is aligned for entry into the ductus Wirsungii 76, which supports the internal structure of the pancreas 73 with all its side branches. Proper alignment is verified through visualization and fiber optics channel 65 of endoscope 64. Then, a small balloon guided catheter 77 is advanced over a guide wire 78 threaded through the side port open channel 67 and out of the side port 72 into the ductus Wirsungii.

Stem cells are delivered and the balloon is inflated by syringes in a method similar to that described with respect to FIGS. 3A and 3B. The distal tip of the catheter is advanced through channel 67 of the endoscope 64 and out of the side port 72 to the site of the pancreatic tissue to be repaired. The catheter's balloon is then inflated through the inflation lumen of the catheter to occlude the Wirsungii duct while stem cells are introduced into the pancreatic tissue through the central lumen of the catheter by proper positioning of the catheter's distal tip at the site of the damaged tissue. Occlusion of the duct prevents stem cells from washing into the intestines, to enhance penetration of cells to the target tissue and large scale adhesions.

If the patient's liver 82 is to be repaired by delivery of stem cells through a natural duct, the distal tip 75 of endoscope 64 is positioned in the duodenum 71 to align its side port 72 for entry into the common biliary duct 80 that supports the liver and the gall bladder 81. Alternatively, the side branch of the bile duct may be used. The guide wire and balloon catheter are fed through channel 67 and out of side port 72 of the endoscope, into the duct. The distal tip of the catheter is positioned at the target site of the liver tissue, the guide wire is removed, and the catheter's balloon is inflated to occlude the biliary duct during introduction of stem cells for adhesion to and engraftment at the failing liver tissue.

The applicants herein have found that the quantity of stem cells required to be injected into the capillary bed is critical to obtaining optimal results. Experiments performed by the applicants have shown that the mean diameter of stem cells derived from subcutaneous adipose tissue is in a range of 11-12 microns. However, this cell size is larger than the size of the capillary bed, which ranges between 5-7 microns. It is essential that stem cells injected to reach a target organ site remain locally and engraft and migrate or cross the intraluminal endothelial lining and become incorporated into the failing tissue of the organ to be repaired.

SUMMARY OF THE INVENTION

It is a principal aim of the present invention to provide an improved method of control of corpuscular fluids that contain particles of a size that ordinarily precludes their passage through the capillary bed, which would otherwise cause an obstruction of the capillary bed.

Measurements and a series of experiments conducted by applicant have shown that the concentration of the cells is also critical. If the cell concentration is low, pressure applied at the injection site can force cells to be forced through the capillary bed and into the systemic circulation, resulting in a reduced effect. This happens, for example, if stem cells are applied in a concentration of less than 1 million per ml. If the concentration, however, is in a range of 2.5 million cells per ml of injection volume, the concentration of stem cells is sufficiently high not to pass through the capillary bed. Too large a number of cells, which involves not only the concentration but the total quantity of cells, applied to the tissue will cause the capillaries to become clogged with these corpuscular structures, result in sudden cessation of the perfusion with blood. Additionally, stem cells in the flow tend to induce certain humoral reactions when the blood flow is reduced. These reactions include an increase in platelet activation, an increase in interaction of platelets with neutrophilic cells, and a release of vessel constrictive factors such as platelet-factor-4 and endothelin, which result in a further vessel constriction downstream.

Variations in the consistency of the cells, the underlying condition of the patient, the size of the damaged tissue of the organ, and the number of capillaries in this specific region make it difficult to determine the quantity of stem cells to be delivered for an optimal therapeutic result.

Parameters such as body weight, age, gender, and other laboratory parameters provide only an indirect link to ascertain the number of cells to be administered to a failing part of the body, such as a certain myocardial area, brain area, hepatic area, renal area, or vascular or subcutaneous locations or substructures of the respective organs. However, through experimental results applicant has found that it is beneficial to use the increase in pressure experienced in the perfused vascular bed as a parameter to determine the number of cells to be injected.

Pressure controlled injections and instrumentation have been used to adapt the injection of fluids to the local conditions, as described in the prior art. An early instrument used to gauge the pressure effect of fluids in a vessel was disclosed in U.S. Pat. No. 4,953,553 to Tremulis, which describes a guide wire with a proximal opening in the main tubular channel to measure pressure in the coronary anatomy. U.S. Pat. No. 6,458,323 to Boekstegers describes a method for selective perfusion of fluids through blood vessels by controlling pressure in the blood vessel. A tubing line open at the proximal end is introduced in the patient's blood vessel for the perfusion of the fluids through a tissue region. Fluid is pumped in the vessel while the vessel is sealed off from the perfusion, and the pressure is regulated during pumping so as to keep the value of the internal pressure for the vessel in a predetermined narrow range. In U.S. Pat. No. 6,039,721, Johnson et al. describe a method and catheter system for delivering medication to a blood vessel with an everting balloon catheter, in which an axial movement of two tubes to used to adjust the length of the balloon by retraction and extension of the tubes against each other. The balloon may be used for sealing the vessel before the medication is applied. And U.S. Pat. No. 6,569,145 to Shmulewitz et al. describes an apparatus and method in which a catheter is used for perfusion of ischemic myocardium. Autoprofusion in the vasculature is controlled by communication with a lumen that controls pressure within an occluded portion of the vasculature and an occlusion element. This prior art, however, describes the injection of fluid in a vessel using a set point of a certain perfusion pressure.

It would be desirable to use conventional equipment to inject the stem cells, but certain limitations of standard equipment make it impractical for this special purpose. Conventional balloon catheters have an inner inflation lumen to accept a guide wire of 0.014 inch, which in principle limits the lumen diameter to less than 0.4 mm. It is feasible to inject the cells through a lumen of such small size; however, considerable pressure is required to overcome the lumen resistance. Use of a syringe and manual injection can produce sufficient pressure to allow a certain percentage of the stem cells to be injected distally of the inflated balloon. But the pressure drop and the pressure needed to overcome the resistance of this small lumen makes it difficult to sense an increase in pressure at the tip of the balloon catheter with a manual syringe injection of a fluid and particles that lead to a continuous or sudden increase in peripheral vascular resistance.

Experiments conducted with human stem cells have shown that after a certain number of cells are infused by intracoronary delivery the myocardial perfusion is considerably compromised, and in the worst case, completely ceases. This phenomenon negatively impacts on the engrafting of the stem cells, which is also dependent on an oxidative metabolism that requires the flow of blood through the capillary bed.

Further, applicants have found that the obstruction of a small vessel such as a coronary artery or an artery in the brain of a human can be significantly impacted if the outer dimension of a perfusion catheter is obstructing a larger part of the vessel. Many vessels in the heart, in the brain, and in other organs of the human body have lumen diameters in a range between 1.5-3 mm. If a catheter with a diameter of roughly 1.1-2 mm is inserted in such a vessel, the perfusion in the extreme case is completely compromised by the presence of the catheter diameter. Hence, a placement of such a catheter for more than 30-50 seconds will not be tolerated without provoking a severe ischemic reaction. Therefore, the diameter of a perfusion catheter should be as small as possible, preferably in a range considerably below 1 mm.

However, this dictates that the inner lumen of such a catheter must be of extremely small diameter, which in turn affects the amount of pressure required to overcome the resistance of such a small catheter in order to start infusion. In previous typical cases of use of a balloon catheter, no consideration has been given for this fact since normally the inner lumen of such a catheter is used only to accept the guide wire. In the instant case, however, the lumen size impacts on the ability to inject an appropriate quantity of stem cells to achieve the desired repair. The pressure required to overcome the resistance presented in this case depends not only on the length, but also on the diameter of the lumen. Here, with a fourth order of the radius according to the Bernoulli equation, to overcome the resistance induced by a 0.14 inch inner lumen necessitates a pressure of roughly 200 mm Hg. However, a catheter with an inner diameter of 1 mm produces a pressure drop of less than 10 mm Hg over the same length.

The present invention is directed to a modified catheter system and method of use thereof that provides a small distal part for insertion into a respective organ artery and its smaller diameter, and, as well, anticipates the requirement for a larger diameter in parts of the catheter that are to be located in the larger vessels such as the aorta and larger branches of the main vessels of the human body.

In addition, the present invention provides a closed loop automatic system and method of use thereof that enables optimal infusion of a prescribed number of stem cells into a failing structure of the human body irrespective of the size and specific conditions of the structure. This enables a close pressure measurement in which a predetermined set value is recognized to terminate the cell infusion. While the system of the applicant's '403 application has shown merit for use of stem cells derived from human subcutaneous adipose tissue which represent primarily mesenchymal stem cells located in the microvasculature such as capillaries and part of what has been described as pericytes, the system and method provided by the catheter and pressure monitored injection capability of the present invention are equally applicable for any type of stem cell derived from the human body including mesenchymal stem cells from non-autologous origin such as embryonic stem cells.

According to a first aspect of the invention, an improved method is provided for repairing tissue of a failing organ in a patient's body. The method includes delivering stem cells of a type having the capability to replace or repair the tissue to the site of the failing organ through a blood vessel or duct of the site, by performing the delivery with pressure controlled infusion of a fluid containing the stem cells intraluminally through a catheter inserted in the vessel or duct, while selectively occluding the vessel or duct upstream during the infusion by selectively inflating a distally affixed balloon on the catheter, and controlling the pressure downstream of the occlusion balloon so as to set the conditions and parameters of delivery of the stem cells including the quantity of stem cells delivered.

The method includes increasing or decreasing the perfusion pressure at the site of the failing organ to control the quantity of cells delivered to the organ.

In the method, the stem cell-containing fluid is intraluminally applied through the catheter, first through a proximal portion of the catheter characterized by a central lumen of designated diameter and length and then through a distal portion characterized by a central lumen of smaller diameter and shorter length than the diameter and length respectively of the proximal portion, the lumina of the two portions communicating with each other to enable the fluid to flow through the entire central lumen of the catheter for ejection into the vessel or duct from the distal tip of the catheter. The method also includes selecting the relative diameters and lengths of the lumina of the proximal and distal portions, toward minimizing the pressure drop of the fluid flow through the catheter.

The method is further enhanced by controlling the pressure and increases or decreases in the pressure of the fluid flow, with a closed loop system coupled to the catheter.

Another aspect of the invention comprises a catheter for infusing stem cells through a vessel or duct of a patient's body to effect a repair of failed tissue of an organ served by the respective vessel or duct. The catheter has a proximal portion of relatively larger central lumen diameter and outer diameter, and a distal portion of relatively smaller central lumen diameter and outer diameter. The two portions are integral with one another so that stem cells delivered into the central lumen of the proximal portion will flow through and exit the central lumen of the distal portion. The relative lumen diameters and lengths of these portions are selected to minimize the pressure drop across the catheter during the infusion.

The catheter includes a balloon positioned on the distal portion adjacent the distal tip of the catheter from which the stem cells are to exit the catheter, and an inflation lumen for the balloon by which the balloon may be selectively inflated and deflated to seal the vessel or duct in which the catheter is inserted, to prevent backflow of the stem cells during their infusion.

As part of the apparatus, a closed loop pressure regulated delivery system is utilized in delivering stem cells into the central lumen of the proximal portion of the catheter, for controlling the pressure and flow of stem cells through the entire central lumen of the catheter including the proximal portion and the distal portion.

According to still another aspect of the invention, a method is provided for infusing stem cells through a catheter, using a catheter that has at least two interconnected lumina as the central lumen of the catheter for the infusion, in which the relative diameters and lengths of the interconnected lumina form at least one constriction in the central lumen of the catheter selected toward minimizing the pressure drop of infusion through the catheter.

In yet another aspect, a method of infusing stem cells through a catheter includes pumping a fluid that contains the stem cells into a lumen of the catheter at its proximal end, and at a preselected point of its travel through the lumen, constricting the diameter of the lumen to increase the flow velocity of the fluid through the catheter from that point and thereby lower the pressure to reduce the pressure drop through the catheter toward zero. Pressure of the fluid exiting from the catheter is regulated by the closed loop system.

BRIEF DESCRIPTION OF THE DRAWINGS

The above and still further aims, objectives, features, aspects and attendant advantages of the present invention will become apparent to those skilled in the art from the following detailed description of a best mode presently contemplated of practicing the invention by reference to certain preferred methods of application thereof, taken in conjunction with the accompanying figures of drawing, in which:

FIGS. 3A and 3B are companion simplified views of syringes used in such a procedure.

FIG. 7A illustrates a presently preferred embodiment of an improved catheter for the adapted infusion of stem cells, to be part of a closed loop automatic system, and useful for describing a method of use thereof, according to the present invention; with FIGS. 7B and 7C illustrating cross-sectional views of the catheter along the lines 7B-7B and 7C-7C, respectively.

DETAILED DESCRIPTION OF THE PRESENTLY CONTEMPLATED BEST MODE OF PRACTICING THE INVENTION

The accompanying Figures of drawing, including FIGS. 1-4 discussed in the Background section above, are not intended to be to scale, nor to do more than serve as a visual aid to the description. In those Figures representing the human body or body parts, certain components may be exaggerated relative to others for the sake of emphasis or clarity of the respective accompanying description.

Figure 1:
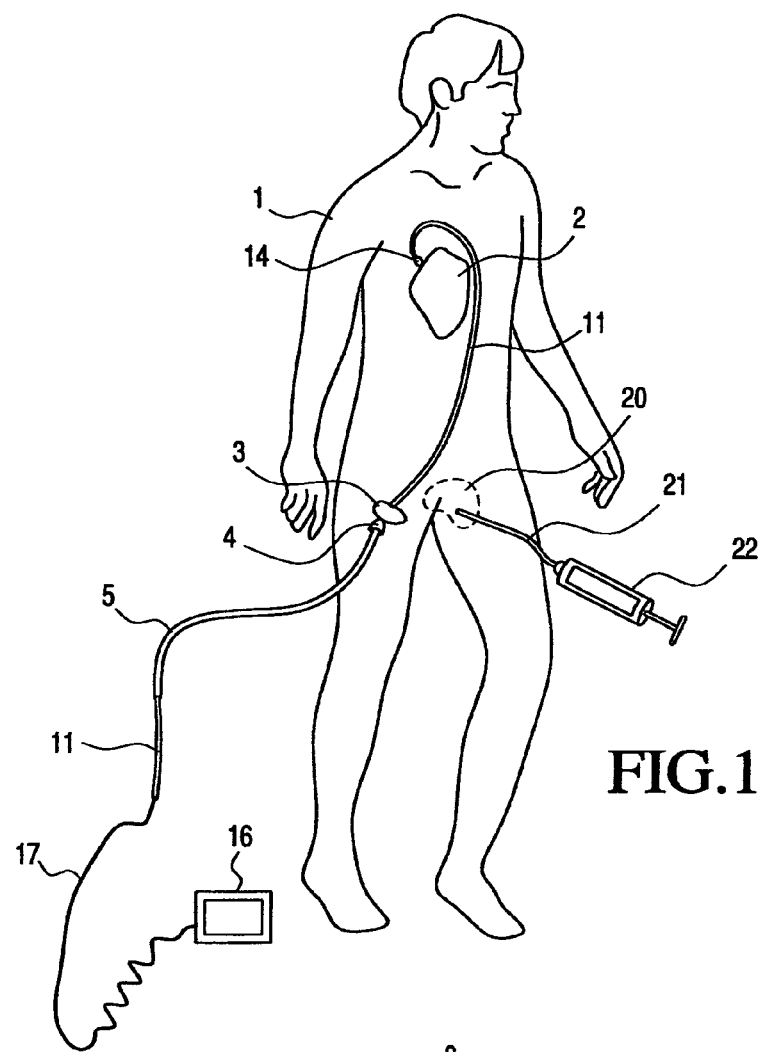
FIG. 1, described above, is a transparent front view of a patient showing exemplary locations for obtaining autologous adult stem cells, and for injecting the harvested stem cells into the cardiovascular system and through a balloon catheter for introduction at the site of myocardial tissue damage to be repaired.
Figure 2:
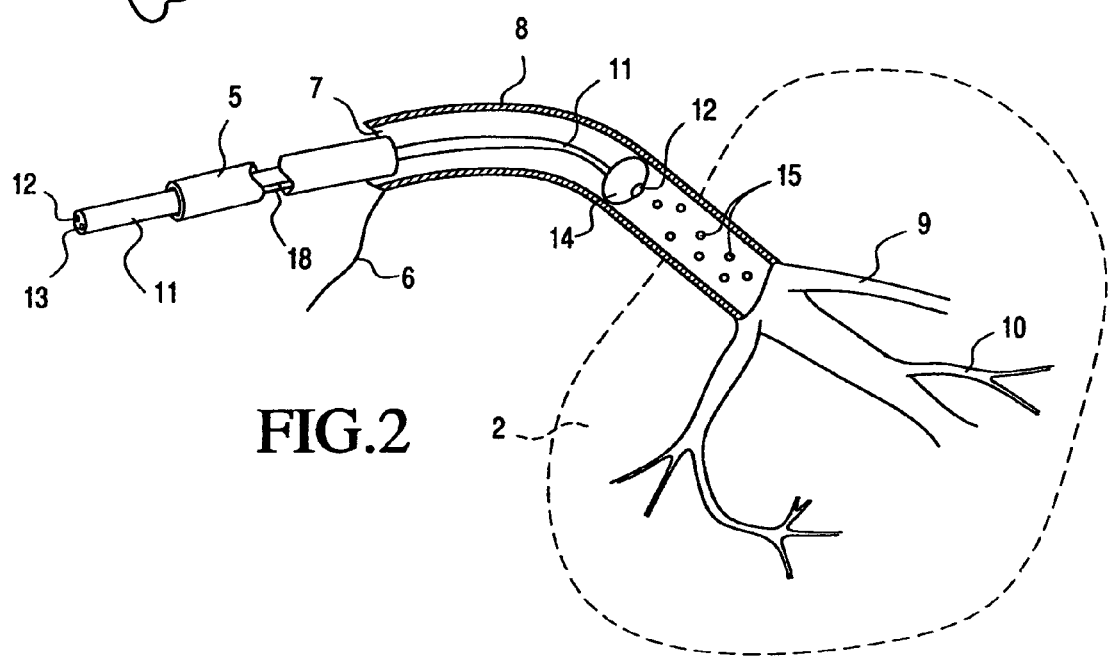
FIG. 2, described above, is a detail view of the injection of cells into the cardiovascular system at the designated site in FIG. 1.
Figure 3:
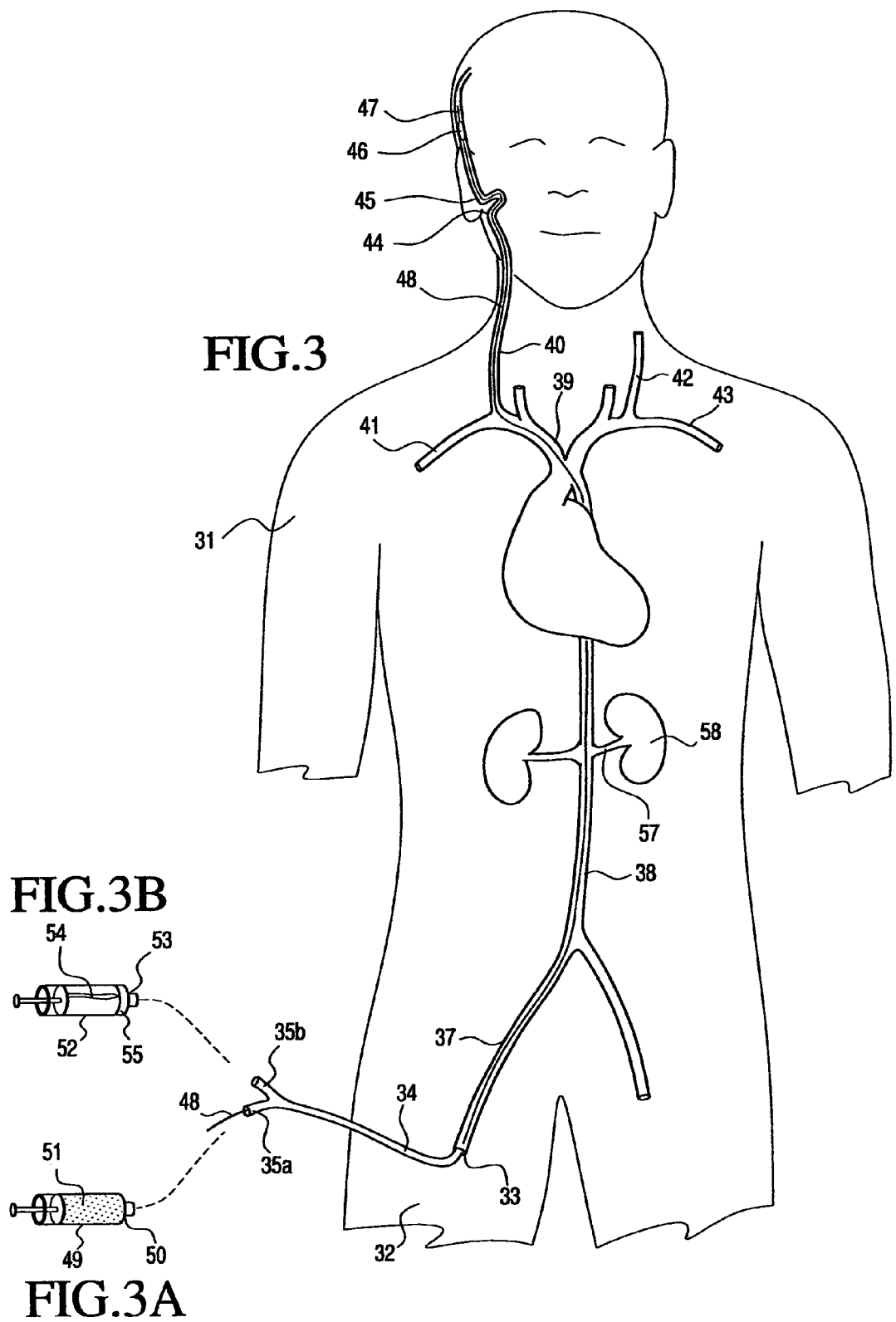
FIG. 3, described above, is a transparent front view of a patient illustrating an exemplary procedure for injecting harvested cells into the cerebral circulation of a patient.
Figure 4:
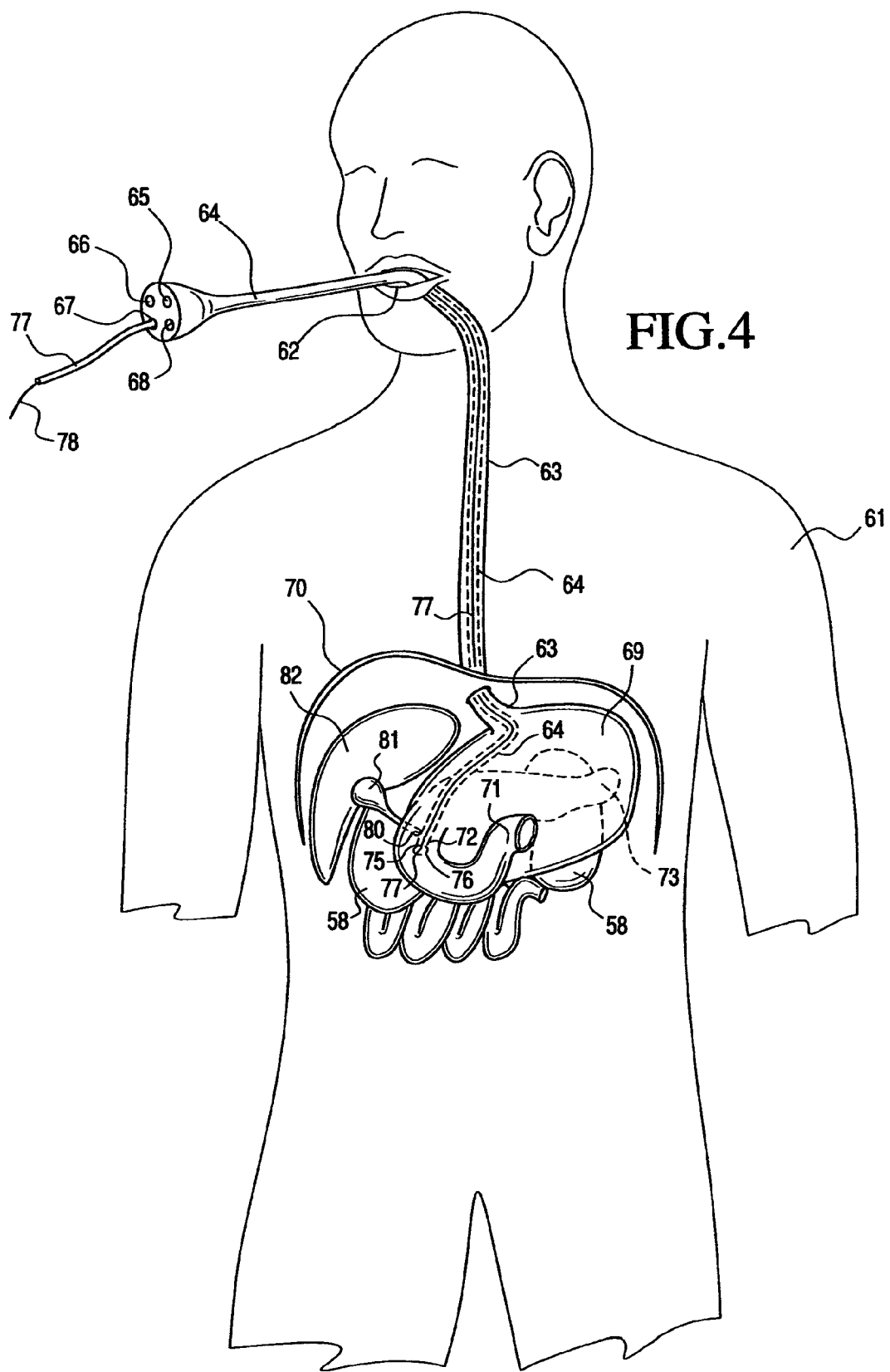
FIG. 4, described above, is a transparent front view of a patient illustrating an exemplary procedure for applying harvested stem cells through a duct of a patient's body, to damaged tissue of an organ such as the pancreas or liver.
Figure 5:
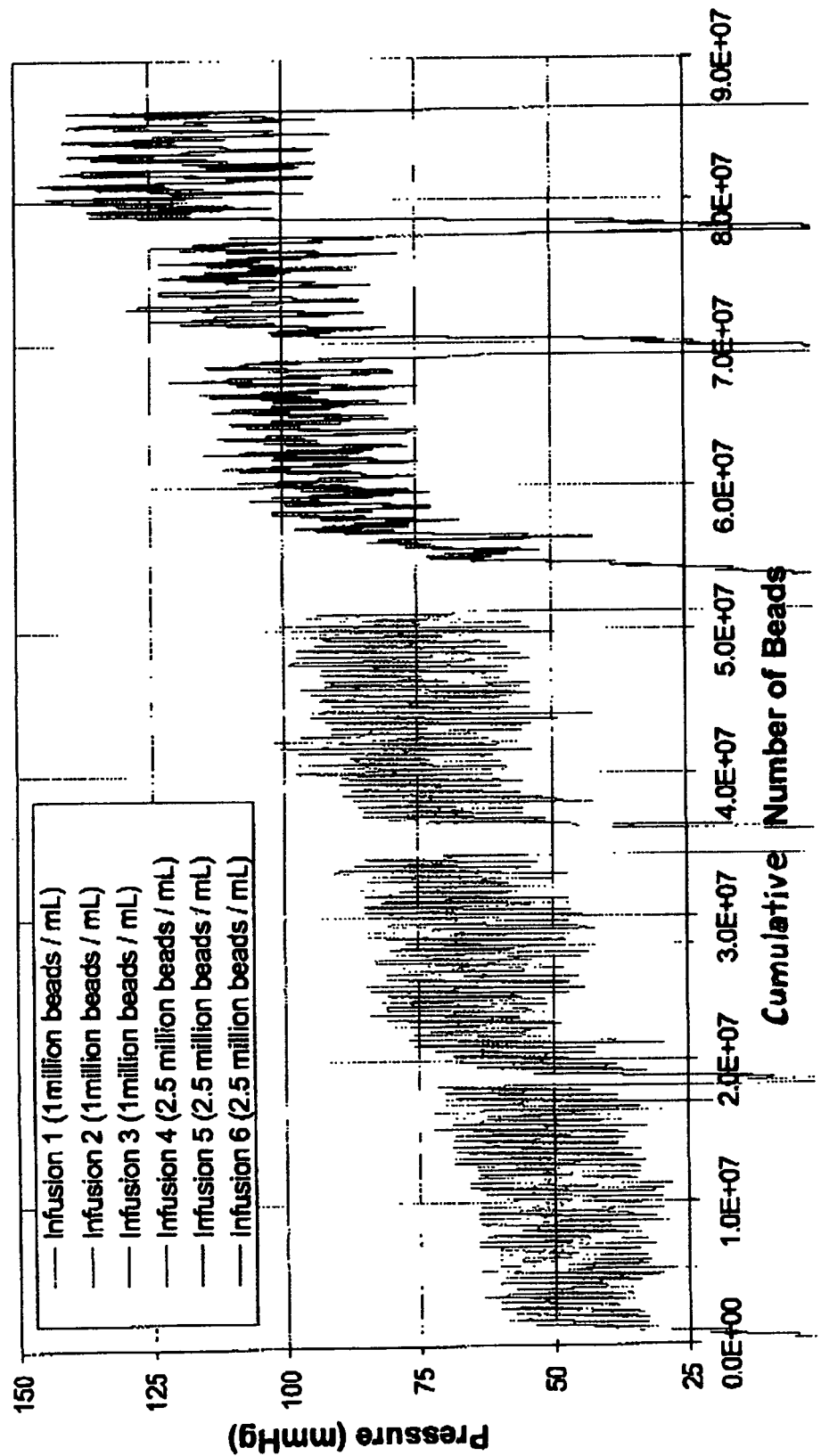
FIG. 5 is a graph that illustrates pressure values and pressure curves that represent catheter tip pressures during infusion of polystyrene microbeads (cumulative in number along the x-axis) in experiments simulating infusion of stem cells.

The basic conditions addressed by the delivery system and method of the present invention (but using conventional apparatus to illustrate the problems sought to be overcome) are illustrated in the graph of FIG. 5, with plots of catheter tip pressures in mm Hg (millimeters of mercury) versus cumulative number of 11.5 μm (micrometer, or micron) diameter polystyrene beads, or microbeads (simulating the size of stem cells for purposes of the experiments conducted by the applicant), infused into a region of body tissue to be repaired.

In conducting the experiments that led to the results shown in FIG. 5, a 0.018 inch inner lumen of a conventional Cordis Corporation over-the-wire-balloon catheter (not shown) was used for infusion of the microbeads into a non-infarcted myocardial area of the mid-left circumflex artery (LCX) of a pig. A pressure monitored infusion pump (not shown in this Figure) was used for initially injecting a solution that contained 1 million microbeads per milliliter (ml) of fluid (saline).

Since the diameter of the microbeads is larger than the diameter of the capillaries, the microbeads become stuck in and clog the capillary bed. The number of microbeads infused continued at a concentration of 1 million per ml until approximately 20 million beads had been injected (infusion 1 on the graph of FIG. 5). Then two more infusions of approximately 16 million beads each in the same concentration (infusions 2 and 3 on the graph) were delivered until a total of about 52 million microbeads had been injected at a concentration of 1 million per ml after placement of the Cordis catheter. In FIG. 5, the pressure values along the y-axis (ordinate) represent the capillary occlusion following the infusion of the cumulative number of microbeads (in the indicated concentrations of microbeads per ml) along the x-axis (abscissa) of the graph, and the pressure curves represent catheter tip pressures during infusion. The results indicate that a mean pressure of about 35-40 mm Hg (with fluctuations in the range of 35-75 mm Hg following the cardiac cycle with systole and diastole) is required to overcome the resistance of the 0.018 inch inner lumen of the catheter to cause the fluid to exit the tip of the catheter.

As the graph indicates, the catheter tip pressure increases with each increase in the cumulative number of microbeads infused. After injection of more than 50 million beads there is not only an exponential rise in pressure, but also the phenomenon of no reflow, which means the normal blood circulation is also compromised such that the respective designated target myocardial tissue is no longer perfused.

The different segments of the graph indicate the pressure at the tip of the catheter after infusion of from about 10-90 million microbeads. After roughly 50 million microbeads were infused, a considerable increase in mean pressure was encountered through the inner lumen of the balloon catheter. At the commencement of infusion, the initial pressure required to achieve a flow varied with heart beat and respiration and averaged about 40 mm Hg, which represents the pressure drop over the length of the catheter that was used.

And a continuous increase in pressure over time and over the number of microbeads infused is shown by the graph. There was roughly an increase of 40 mm Hg from the start of the infusion to the first approximately 50 million microbeads that were injected. Beyond the first approximately 50 million microbeads injection, the concentration of microbeads was then increased to 2.5 million per ml, and a further increase in pressure by more than 60 mm Hg up to a mean of 120 mm Hg with considerable cyclic variables by the heart and ventilation is observed at the catheter tip, which indicated that the capillary circulatory system (bed) was now blocked with roughly 90 million microbeads.

Figure 6A:
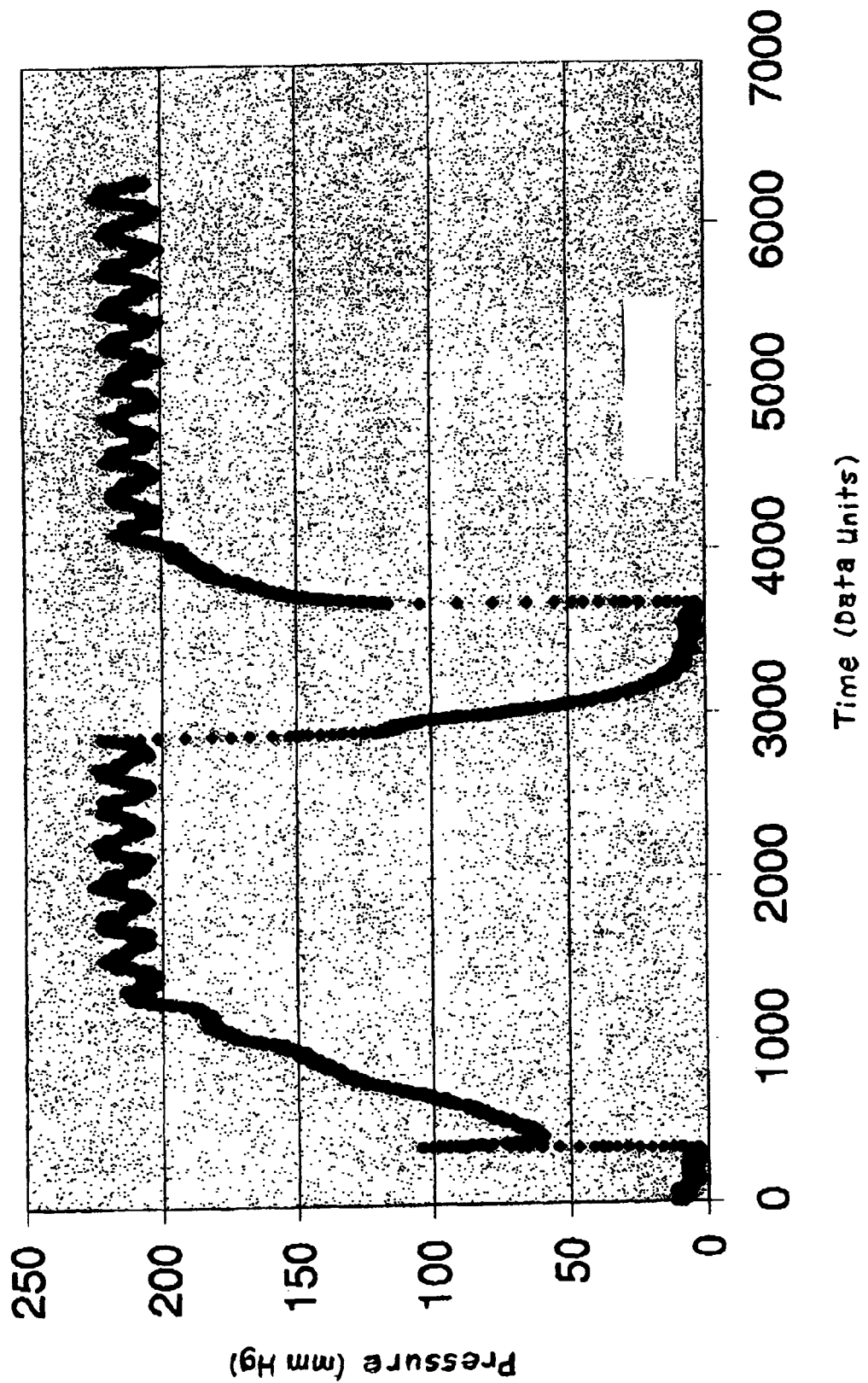
FIG. 6A is a graph of the start, stop, and start again of the saline infusion baseline illustrating the pressure increase needed with a small catheter of 0.014 inch diameter lumen, to achieve a constant flow of only saline (without stem cells) at a rate of 3 ml per minute indicating a constant distal pressure.

FIG. 6A is a graph of the start, stop, and start again of the saline infusion baseline for a smaller catheter of 0.014 inch diameter lumen, to achieve a constant flow of only saline (without stem cells) at a rate of 3 ml per minute indicating a constant distal pressure. This Figure illustrates the increased pressure required to infuse through the smaller diameter catheter, with the ordinate representing pressure in units of mm Hg, and the abscissa representing data units of time. The higher pressure requirement is attributable to the change in catheter lumen diameter. In contrast to the roughly 40 mm Hg required to overcome the resistance for fluid to exit the tip of the 0.18 inch diameter lumen catheter used in experiments that produced FIG. 5, it is seen that more than 200 mm Hg of pressure was required to overcome the resistance at the tip of the 0.14 inch lumen catheter. On the other hand, because of its smaller outer diameter as well, the latter catheter blocks less of the vascular cross section, with a consequent lower impact on the normal blood flow when placed in the coronary system, making it preferable to the larger diameter catheter for the infusion process through a blood vessel. The variations in pressure shown in the graph of FIG. 6A represent the effects of ventilation and heart beat, and indicate the perfusion pressure variations with those factors.

The drop in pressure that occurred at a time point of roughly 3300 indicates that the infusion has ceased, while the increase that takes place at about 3600 data units of time illustrates the rise in pressure to resume the transport of saline infusion. It is also readily seen from the graph that the pressure level throughout the infusion is relatively stable with little or no increase (other than the variations that occur as a result of the factors noted above), which is attributable to the saline containing no microbeads being easily washed though the capillary perfusion of the organ.

Figure 6B:
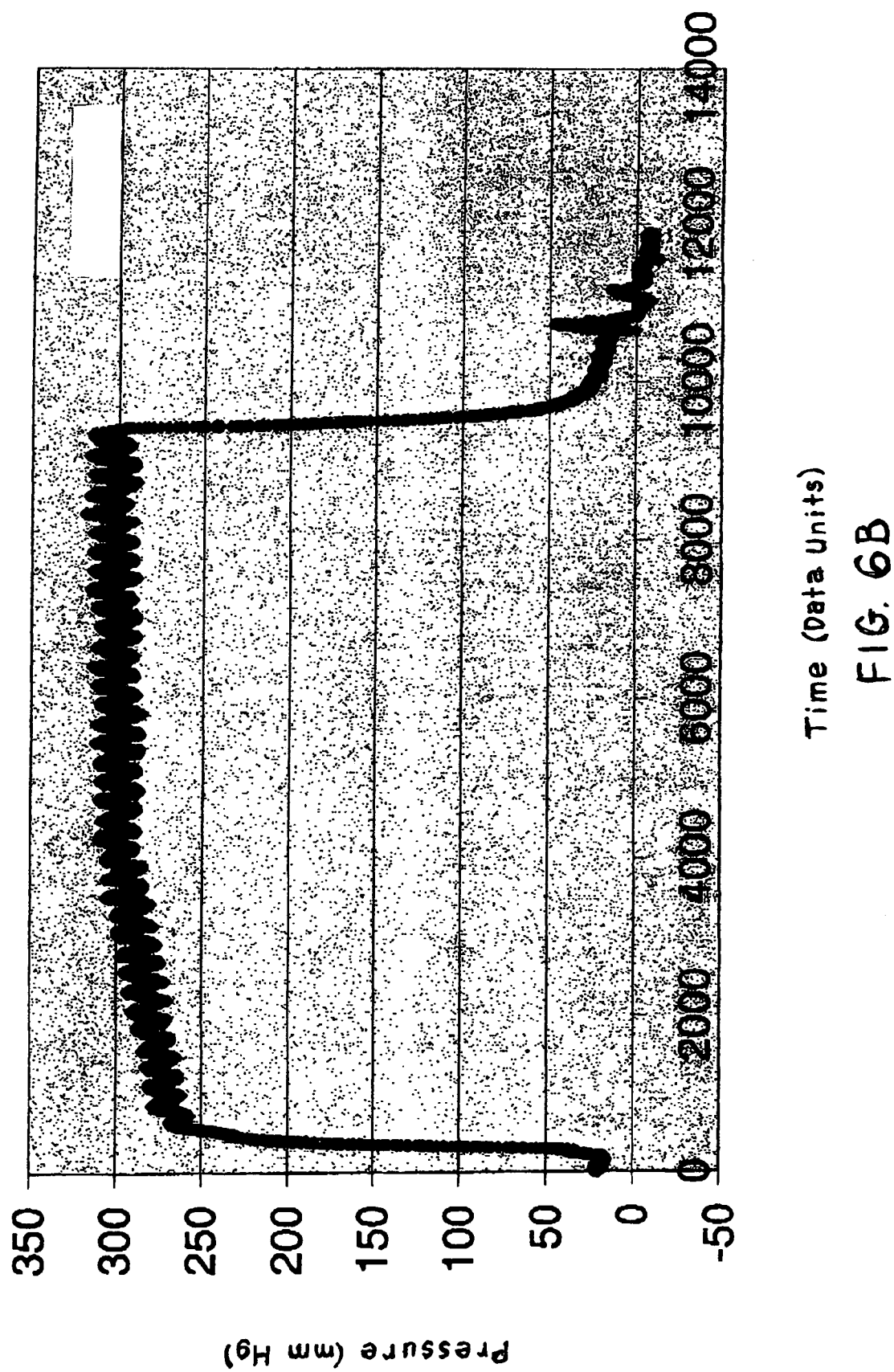
FIG. 6B is a graph illustrating the increase in pressure over time when microbeads are injected at a rate of 3 ml per minute.

FIG. 6B illustrates the results of a different experiment, namely, the increase in pressure over time that occurs with injection of microbeads, simulating injection of stem cells, at a rate of 3 ml per minute. Here again, the ordinate represents pressure in units of mm Hg, and the abscissa represents data units of time, the difference from FIG. A being that the former resulted from infusion of fluid, specifically saline only, whereas the graph of FIG. B indicates injection of corpuscles or particles such as microbeads (or stem cells). In the latter experiment or example, the pressure rose to a level of roughly 300 mm Hg. That is, the resistance in the microvasculature increases because of a continued filling of microbeads or stem cells. The initial jump in pressure arises from a relatively rapid increase in obstruction of the capillary bed, and the difference of roughly 50 mm Hg in increased pressure from just after the start to the stop of the injection is offset by a more than 250 mm Hg pressure drop over the length of the catheter. The increase over the initial perfusion pressure levels off to roughly 300 mm Hg because at that high pressure the microbeads are squeezed and transported through the capillary system. This is an undesirable result because the intent of the procedure is that stem cells be injected primarily into the target organ designated to be repaired, to engraft and remain there, rather than being squeezed at high pressure through the capillary bed.

Attention is now directed to FIG. 7A, which illustrates a presently preferred embodiment of an improved catheter, together with a portion of a closed loop automatic system (more fully described in the discussion of FIG. 8 below) according to the present invention. Catheter 100 comprises a proximal portion of tubing 101 having a predetermined diameter (discussed below) and a length of approximately 120 cm. In describing this embodiment, it will be understood that dimensions are provided merely by way of example and are not to be taken as limiting the principles of the invention. A more distal portion 102 of the tubing of catheter 100 has a length in a range of from about 10 cm to about 30 cm and a smaller diameter (relative to that of portion 101) sized to fit through a smaller vessel lumen at the target organ where the cells are to be delivered. The lengths and diameters of catheter 100 portions 101 and 102 are selected so as to avoid compromising and obstructing the respective vessel or duct into whose lumen they are to be inserted.

For example, catheter portion 101 is sized to be inserted into one of the relatively larger arteries among the arteries in the human body, such as the femoral artery, aorta, brachial or carotid artery, all of which have a diameter typically in a range of from about 4 to about 10 mm. Therefore, lumen 106 of catheter proximal portion 101 (FIGS. 7A, 7B) has a diameter in a range of from about 1 mm to about 2 mm (and tubing portion 101 has a concomitant outer diameter) that will not obstruct the artery in which it is placed but will allow perfusion therethrough with corpuscular fluid such as a stem cell-containing solution.

And lumen 105 of the distal portion 102 (FIGS. 7A, 7C) has a relatively smaller diameter, in a range from 0.014 inch to 0.021 inch (with a concomitant diameter of the distal portion itself), than lumen 106 of proximal portion 101 of catheter 100. The particular diameter size of lumen 105 is selected as appropriate according to the diameter of the relatively small vessel or duct leading to the target organ to be treated by injection of stem cells from the catheter. The central lumen of catheter 100 is continuous, with proximal lumen 106 running directly into distal, albeit smaller, lumen 105.

For use in an infusion into the brain, for example, distal portion 102 may be sized with a lumen diameter of 0.014 inch (about 0.35 mm), which is suitable for insertion into an appropriate artery for the treatment (i.e., the anterior cerebral artery) since the outer diameter of that potion of the catheter would then be in a range below 0.65 mm and would not obstruct even such small vessels. For use in slightly larger arteries (e.g., with a lumen diameter of 2 to 3 mm), the distal portion 102 of catheter 100 may be sized with a lumen diameter of 0.018 inch to 0.021 inch, since the outer diameter of portion 102 would then be in a range of roughly 0.8 mm to 1 mm.

Thus, if the catheter 100 is to be used for infusion of stem cells into a relatively large diameter lumen vessel or duct, the distal portion 102 is readily inserted and the proximal portion 101 can also be inserted without undue obstruction of the lumen of the vessel or duct. And if the catheter is to be used for infusion of stem cells into a relatively small diameter lumen vessel or duct, the distal portion 102 may be inserted for delivery of the stem cells without need to insert the proximal portion 101 beyond the point at which the smaller vessel or duct departs from the larger one (or to any point at which obstruction of the lumen might occur).

Among the principal aims of the invention are to provide means and method to minimize the pressure drop of the stem cell infusion catheter, from the point of ingress of the fluid that contains the stem cells at the catheter inlet to the point of egress at the catheter distal tip. Doing so assures that instead of producing a high pressure that tends to cause squeezing and clogging of the capillary system as the stem cells are delivered thereto (as seen from the experimental results obtained with respect to the examples of FIGS. 6A and 6B), the stem cells are injected primarily into the target organ to be repaired, to engraft and remain there. This is achieved by use of the catheter 100, and more generally by a catheter dimensioned with a length of larger diameter central lumen at its proximal end and with a length of smaller diameter central lumen at its distal end, preferably with the larger diameter proximal length being substantially longer than the smaller diameter distal length.

With continuing reference to FIG. 7A, a pump 108 is connected at the proximal entry point of catheter 100 to deliver fluid containing the stem cells into the central lumen 106 of proximal tubing length 101 and thence into central lumen 105 of distal tubing length 102. The stem cells are thereby ejected from the catheter's distal tip and through the artery or duct into which the catheter tip is inserted that leads to the target organ for infusion, with perfusion across the capillary bed.

In addition to the central lumen of the catheter with its proximal and distal portions 106, 105, a separate channel 103, which may at some point be incorporated into the wall of catheter 100 (as shown), is arranged and adapted for connection at its proximal end to an inflation pump 109. At its distal end channel 103 opens into a balloon 104 affixed adjacent to the distal tip of the catheter. The balloon 104 may thus be selectively inflated and deflated, preferably using a 50/50 mixture of saline and contrast dye as the inflation fluid, from and to the pump 109 through the channel 103. Inflating the balloon serves to proximally seal the vessel or duct in which the catheter is inserted, as the stem cells are slowly ejected from pump 108 into and through the central lumen of the catheter. The cells are thereby ejected from the catheter tip for infusion into the target organ, while they are prevented from undergoing backwash past the location of the sealed region during the infusion procedure. The period of inflation is monitored and maintained sufficient short to preclude damage to the organ tissue from blockage of blood flow.

A pressure transducer 110 controls the delivery and withdrawal of the inflation fluid by pump 109 through lumen 107 (FIGS. 7B, 7C) of channel 103. The diameter of lumen 107 is small, preferably about 0.15 mm, so that it adds very little to the total diameter of catheter 100 from the point where they are integral with each other.

Whether the catheter is placed within a small diameter lumen or a large diameter lumen vessel or duct for infusion of the stem cells, the balloon 104 is inflated to the extent necessary to achieve a tight seal, and deflated promptly after the desired quantity of stem cells has been injected.

As noted hereinabove, the lumen size of the catheter impacts on the capability to inject an appropriate quantity of stem cells to achieve the desired repair of the target organ. The pressure required to overcome the resistance presented by the catheter tip depends not only on the length, but also on the diameter of the lumen. The exit from the catheter tip at the central distal lumen 105 is represented by the fourth order of the radius according to the Bernoulli equation, which effectively states that the total energy (pressure plus gravitational plus kinetic energy) is constant, with the implication that the pressure falls where the fluid flows faster and visa-versa. The Bernoulli effect is a reduction of fluid pressure in regions where the flow velocity is increased. Looking at a reduced pressure that occurs in a constriction of a flow path in terms of pressure as being energy density, tends to clarify the realization that for high velocity flow through the constriction, kinetic energy is increased with a tradeoff of lowered pressure energy.

This means that the pressure drop that occurs over the length of the central lumen of a catheter exemplified by the embodiment of FIG. 7A, for the respective lengths and radii of its two component lumens 106 and 105, is relatively small. And this is a highly desirable effect where the catheter is to be used in a procedure involving delivery of stem cells to the site of organ damage to be repaired. Supplementing the structure of the catheter 100 that serves to reduce the pressure drop, the pump 108 is connected to a pressure transducer 111 and circuitry (FIG. 8, discussed below) to control an increase in perfusion pressure over the pressure needed to generate flow. The pressure transducer 111 measures the pressure in the perfusion system including catheter 100 and pump 108 to which the transducer is connected.

Figure 8:
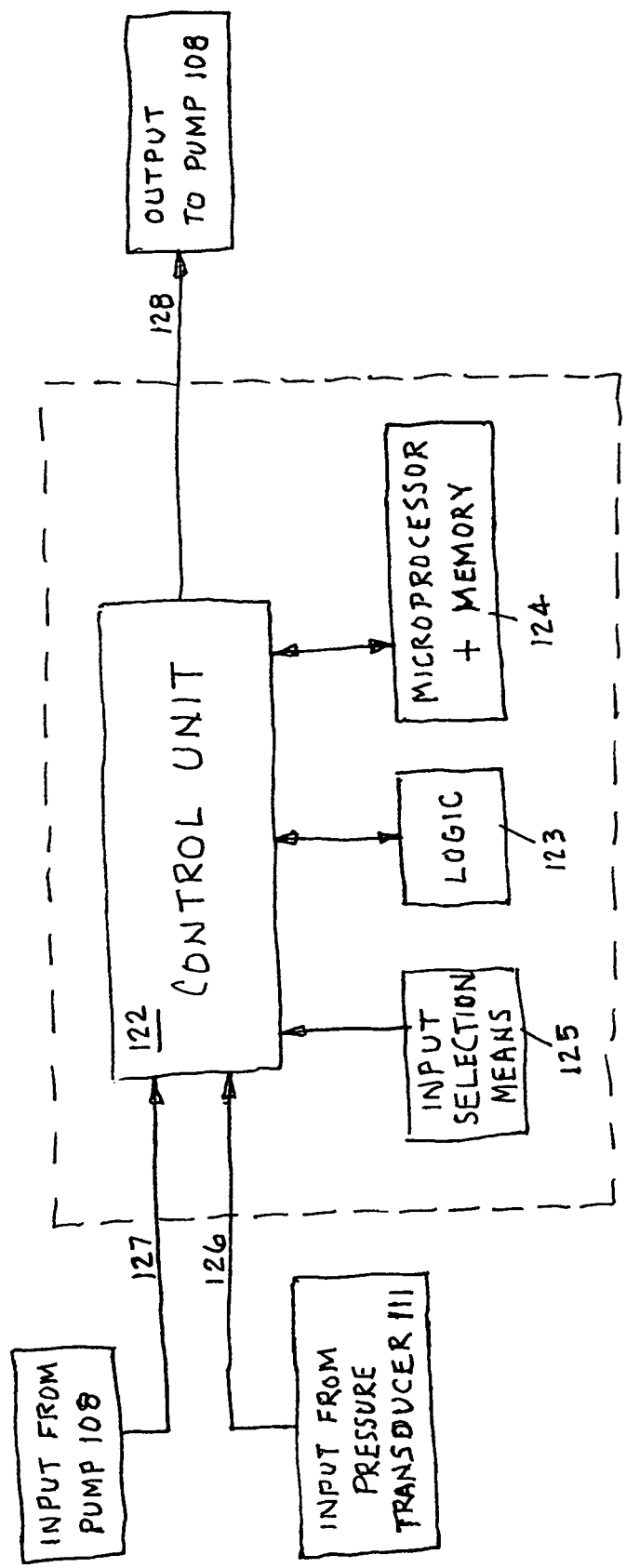
FIG. 8 is a block diagram of an embodiment of a pressure controlled, closed loop system according to the invention, in which the improved catheter of the invention is operated for stem cell repair of an organ's failing tissue.

Referring now to FIG. 8, a block diagram of a preferred embodiment of a pressure controlled, closed loop system, transducer 111 reports the measured pressure as an input 126 to a control unit 122. Control unit 122 comprises a logic circuit 123, a microprocessor with associated memory 124, and an input selection means 125. Information for the closed loop regulation of pressure in the system is received from the pressure transducer via input 126 and also as an input 127 from pump 108. The data from pump 108 and pressure transducer 111 are processed according to the settings on input selection means 125 of the variables of pressure, pressure increase and flow for a given catheter, stem cell or corpuscular solution and patient, together with the logic 123 and microprocessor 124 entries, at the control unit 122. An output 128 of control unit 122 to pump 108 regulates the flow and the increase in pressure of the stem cell solution delivered by pump 108 to catheter 100.

For repairing an organ by infusion of stem cells, a maximum rise in pressure and a maximum pressure are selected. The delta of the pressure increase over the baseline perfusion pressure depends on the viscosity of the fluid containing the stem cells, the length of the catheter through which the cells are to be infused, the composition of the catheter, the size of the perfilvascular bed, the tight sealing of the balloon at end of the catheter 100, and on the underlying hematocryte and viscosity of the blood. With these factors a respective increase in the rise of the pressure is set that indicates when sufficient stem cells are delivered to effect repair of the designated organ.

Control of the number of cells delivered and the pressure applied for the infusion is particularly important for organs having tissues that exhibit relatively lower physical stability and firmness. Organs where such tissue parameters are more solid, such as the heart, are unlikely to experience deleterious effects from extravasation. This is because in the heart, for example, the myocardial cells are very firmly connected to each other with little space between them. In contrast, some organs, such as the brain, may suffer certain ill effects as a result of extravasation, such as hemorrhaging because of the consistency of their cellular structure. Accordingly, in treating organs of the latter type, careful control of the number of cells injected and the pressure applied for doing so takes on even greater importance.

The pressure control achieved through the catheter's central perfusion lumen with a closed loop system such as the embodiment of FIG. 8 may be further assisted by means of a pressure sensor located at the distal tip of the catheter. The pressure sensor or transducer may comprise a fiber that runs parallel to the lumina 106 and 107 from the proximal end to the distal tip of catheter 100. The detected pressure information is then fed to the control unit 122 together with the input from pressure transducer 111 on line 126.

Although a presently contemplated best mode of practicing the invention has been closed by reference to certain preferred methods, it will be apparent to those skilled in the art from a consideration of the foregoing description that variations and modifications may be made without departing from the spirit and scope of the invention. Accordingly, it is intended that the invention shall be limited only by the appended claims and the rules and principles of applicable law.

What is claimed is:

1. A method of delivering stem cells to a failing organ in a patient's body, comprising:
    selecting a catheter dimensioned for a selected failing organ, wherein the catheter comprises a proximal portion and a distal portion and has a continuous central lumen extending from the proximal portion into the distal portion, wherein the diameter of the lumen in the distal portion is smaller than the diameter of the lumen in the proximal portion, and wherein an outer diameter of the distal portion is dimensioned to fit into a duct or vessel of the failing organ to a target site of damaged tissue of the failing organ;
    inserting the selected catheter into the duct or vessel of the failing organ and advancing the catheter to a location proximate the target site;
    occluding the duct or vessel upstream of the target site by inflating a distally affixed balloon on the catheter;
    injecting under a selected desired pressure a fluid containing stem cells through the catheter for ejection under pressure from the central lumen at the distal tip of the catheter proximate the target site, while measuring the injection pressure; and
    adjusting the injection pressure of the fluid containing the stem cells flowing through the catheter to the selected desired pressure by a closed loop system coupled to the catheter.

2. A method as defined in claim 1, wherein adjusting the injection pressure comprises reducing the injection pressure of the fluid if the measured injection pressure is greater than the selected desired pressure, and increasing the injection pressure of the fluid if the measured injection pressure is less than the selected desired pressure.

3. A method as defined in claim 1, wherein the catheter has a proximal portion comprising a central lumen of about 1 to about 2 millimeters in diameter and a distal portion comprising a central lumen of about 0.014 to about 0.021 inches in diameter.

4. A method as defined in claim 1, wherein the closed loop system comprises:
    a pressure transducer adapted to generate an output associated with the measured injection pressure;
    a pump operatively coupled to the catheter and adapted to control the injection pressure of the fluid through the catheter; and
    a control unit comprising a microprocessor having a memory, operatively coupled to the pressure transducer and the pump to receive the output associated with the measured injection pressure and to regulate control by the pump to increase or decrease the injection pressure of the fluid through the catheter to maintain the selected desired pressure.

5. A method as defined in claim 1, wherein the duct is a pancreatic, hepatic or biliary duct.

6. A method as defined in claim 1, wherein the length of the distal portion is shorter than the length of the proximal portion.

7. A method as defined in claim 1, wherein the outer diameter of the distal portion is less than or equal to 1 mm.

8. A method as defined in claim 6, wherein the length of the distal portion is in a range from about 10 to about 30 centimeters.

9. A method as defined in claim 4, further including sensing the ejection pressure of the fluid at the distal tip of the catheter and feeding the sensed ejection pressure information to the control unit to assist in adjusting the injection pressure to the selected desired pressure.

10. A method for delivering therapeutic cells to an organ of a patient's body comprising:
    delivering the therapeutic cells through a vessel or duct of the body to a target site of the organ;
    performing the delivery by pressure-controlled infusion of a fluid containing the therapeutic cells through a mechanism for intraluminal application having an outlet proximal to the target site while selectively blocking antegrade flow of blood or ductal fluid and retrograde flow of therapeutic cells proximal to the outlet through the respective vessel or duct; and
    adjusting the infusion pressure of the cell-containing fluid flowing from the mechanism outlet to enable the therapeutic cells being delivered to the organ to overcome an endothelial barrier and reach the organ at the target site for treatment thereof, while limiting pressure drop of the cell-containing fluid through the mechanism;
    wherein adjusting the infusion pressure is performed in a closed system by sensing the infusion pressure of the cell-containing fluid at a location along its travel through the mechanism, comparing the sensed infusion pressure to a selected desired pressure at that location, and regulating the pressure-controlled infusion to maintain the selected desired pressure upon any deviation therefrom at said location and thereby, to maintain the infusion pressure of the cell-containing fluid flowing from the mechanism outlet.

11. The method of claim 10, wherein the mechanism is a balloon catheter having a continuous central lumen for the infusion of the cell-containing fluid, and a separate inflation lumen for a distally-affixed balloon of the catheter for tight sealing of the vessel or duct upon inflation of the balloon so as to perform said blockage.

12. The method of claim 11, wherein the central lumen has a constriction between the proximal portion and the distal portion of the catheter formed by a relatively smaller central lumen diameter of the distal portion than the central lumen diameter of the proximal portion, the relative diameters of the central lumen in the proximal and distal portions being selected to limit the pressure drop of the fluid flowing through the catheter at the constriction.

13. The method of claim 12, wherein the outer diameter of the distal portion of the catheter is relatively smaller than the outer diameter of the proximal portion, to an extent consistent with the relative diameters of the central lumen in the distal and proximal portions, to enable the distal portion to be advanced into relatively smaller diameter vessels and ducts than could accommodate the proximal portion, in close proximity to the target site.

14. The method of claim 10, wherein the therapeutic cells are stem cells.

15. The method of claim 10, wherein the therapeutic cells are adult stem cells.

16. The method of claim 10, wherein the therapeutic cells used for the delivery are autologous adult stem cells.

17. The method of claim 10, wherein the failing organ is the patient's heart, and the vessel through which the therapeutic cells are delivered to the target site is a coronary artery or vein.

18. The method of claim 10, wherein the failing organ is the patient's kidney, and the vessel through which the therapeutic cells are delivered to the target site includes a vascular sequence comprising the iliac artery, the abdominal aorta, and the applicable renal artery.

19. The method of claim 10, wherein the failing organ is the patient's brain, and the vessel through which the therapeutic cells are delivered to the target site is the anterior cerebral artery for introduction into the cerebral circulation.

20. The method of claim 10, wherein the failing organ is the patient's pancreas, and the duct through which the therapeutic cells are delivered to the target site is the ductus Wirsungii.

21. The method of claim 10, wherein the failing organ is the patient's liver, the duct through which the therapeutic cells are delivered to the target site is the bile duct.

22. A method of delivering repair cells to damaged tissue of a failing organ in a patient's body, comprising:
    advancing the tip of the distal portion of a catheter into a vessel or duct of the failing organ to a position proximate a target site of the damaged tissue;
    delivering the cells via pressure-controlled injection of a fluid containing the repair cells proximally through a central lumen of the catheter to eject the fluid from an outlet of the central lumen at the distal tip under pressure, while occluding the vessel or duct proximally of the distal tip during said injection to direct the ejected fluid onto the target site with minimal backflow; and
    regulating the pressure-controlled injection to maintain the pressure of the ejected fluid at a predetermined level so as to overcome a barrier presented by an endothelial lining at the target site and to enable treatment of underlying damaged tissue thereat by the repair cells;
    wherein regulating the pressure-controlled injection is performed by detecting the pressure at an injection site, comparing the detected pressure to a selected desired pressure level at said injection site, and adjusting the injection pressure at said injection site so as to eliminate any deviation from the selected desired pressure level thereat, and thereby concomitantly maintain the pressure of the ejected fluid at said predetermined level; and wherein the detecting, comparing and adjusting are performed with a closed loop system operatively coupled to the catheter; and
    wherein the central lumen has a first diameter in a proximal portion of the catheter and a second smaller diameter in the remaining distal portion of the catheter, thereby forming a constriction between the two at which the fluid flowing therethrough undergoes an increase in velocity and a concomitant decrease in pressure, and the relative sizes of the first and second diameters are selected to reduce a pressure drop of the flowing fluid between its entry at the proximal end and ejection at the distal tip of the catheter.

23. The method of claim 22, wherein the outer diameter of the distal portion of the catheter is relatively smaller than the outer diameter of the proximal portion, accommodating the relative sizes of the first and second diameters of the central lumen, such that the distal portion fits into relatively smaller diameter vessels or ducts than the proximal portion, to enable the distal portion to be advanced into close proximity to the target site of damaged tissue of a failing organ having a relatively small diameter vessel or duct thereto.

24. The method of claim 22, wherein the repair cells are autologous adult stem cells.

25. A method of delivering relatively freshly harvested therapeutic cells to a failing organ in a patient's body, comprising:
    selecting a mechanism dimensioned for transluminal application of the therapeutic cells to the failing organ;
    inserting the selected mechanism into the duct or vessel of the failing organ and advancing a distal end of the mechanism to a location proximate a target site of damaged tissue of the failing organ;
    occluding the duct or vessel upstream of the target site by deploying a distally affixed portion of the mechanism;
    injecting under a selected desired pressure a fluid containing the therapeutic cells through the mechanism for pressurized transluminal ejection of the fluid from the distal end of the mechanism proximate the target site, while measuring the injection pressure; and
    adjusting the injection pressure of the fluid containing the therapeutic cells to the selected desired pressure to compensate for any deviation of the measured injection pressure from the selected desired pressure by a closed loop system so as to maintain the pressurized ejection of the fluid substantially constant, while concomitantly limiting the pressure drop of the fluid from injection to ejection thereof through the mechanism.

* * * * *